(12) United States Patent
Suzuki et al.

(10) Patent No.: US 8,545,382 B2
(45) Date of Patent: Oct. 1, 2013

(54) METHOD OF BALLOON PUMPING AND A BALLOON PUMP DRIVING APPARATUS

(75) Inventors: Akira Suzuki, Nishio (JP); Hideaki Yamaguchi, Toyota (JP)

(73) Assignee: Senko Medical Instrument Mfg. Co., Ltd., Tokyo (JP)

( * ) Notice: Subject to any disclaimer, the term of this patent is extended or adjusted under 35 U.S.C. 154(b) by 354 days.

(21) Appl. No.: 12/211,485

(22) Filed: Sep. 16, 2008

(65) Prior Publication Data

US 2009/0012467 A1   Jan. 8, 2009

Related U.S. Application Data

(63) Continuation of application No. 10/864,606, filed on Jun. 10, 2004, now abandoned.

(30) Foreign Application Priority Data

Jun. 11, 2003 (JP) .................... 2003-166734

(51) Int. Cl.
*A61N 1/362* (2006.01)
(52) U.S. Cl.
USPC ........................................................ 600/18
(58) Field of Classification Search
None
See application file for complete search history.

(56) References Cited

U.S. PATENT DOCUMENTS

| | | | |
|---|---|---|---|
| 4,556,997 A | 12/1985 | Takamiya et al. | |
| 4,832,005 A | 5/1989 | Takamiya et al. | |
| 5,344,398 A | 9/1994 | Hara | |
| 5,817,001 A | 10/1998 | Leschinsky et al. | |
| 5,913,814 A | 6/1999 | Zantos | |
| 6,045,496 A | 4/2000 | Pacella et al. | |
| 6,082,105 A | 7/2000 | Miyata | |
| 6,098,405 A | 8/2000 | Miyata et al. | |
| 6,186,149 B1 | 2/2001 | Pacella et al. | |
| 6,458,323 B1 | 10/2002 | Boekstegers | |
| 6,522,926 B1 | 2/2003 | Kieval et al. | |
| 6,669,624 B2 | 12/2003 | Frazier | |
| 6,850,801 B2 | 2/2005 | Kieval et al. | |
| 6,985,774 B2 | 1/2006 | Kieval et al. | |
| 2001/0005791 A1 | 6/2001 | Ginsburg et al. | |
| 2001/0047196 A1 | 11/2001 | Ginsburg et al. | |
| 2002/0103454 A1 | 8/2002 | Sackner et al. | |
| 2003/0044315 A1 | 3/2003 | Boekstegers | |
| 2003/0060848 A1 | 3/2003 | Kieval et al. | |
| 2003/0060857 A1 | 3/2003 | Perrson et al. | |
| 2003/0060858 A1 | 3/2003 | Kieval et al. | |

FOREIGN PATENT DOCUMENTS

| | | |
|---|---|---|
| JP | 62-224361 | 10/1987 |
| JP | 62-227364 | 10/1987 |
| JP | 63-9447 | 1/1988 |
| JP | 5-16870 | 3/1993 |
| JP | 9-140786 | 6/1997 |
| JP | 9-168596 | 6/1997 |
| JP | 10-328296 | 12/1998 |
| JP | 2002-11093 | 1/2002 |
| JP | 2003-504160 | 2/2003 |
| WO | WO 01/05446 A1 | 1/2001 |

OTHER PUBLICATIONS

Office Action issued May 27, 2008 in Japan Application No. 2003-166734 (With English Translation).

*Primary Examiner* — Christopher D Koharski
*Assistant Examiner* — Elizabeth K So
(74) *Attorney, Agent, or Firm* — Oblon, Spivak, McClelland, Maier & Neustadt, L.L.P.

(57) ABSTRACT

A balloon pumping method of inflating and deflating a balloon includes the steps of setting a pressure in the balloon at a first pressure value, which is higher than a minimum pressure value and is substantially equal to or lower than a maximum pressure value, when the balloon is shifted from a deflated condition to an inflated condition, and setting the pressure in the balloon at a second pressure value, which is substantially equal to or higher than the minimum pressure value and lower than the first pressure value, when the balloon is estimated to have completely inflated at the first pressure value.

9 Claims, 15 Drawing Sheets

METHOD OF BALLOON PUMPING AND A BALLOON PUMP DRIVING APPARATUS

CROSS REFERENCE TO RELATED APPLICATIONS

This application is based on and claims priority under 35 U.S.C. §119 with respect to Japanese Patent Application 2003-166734, filed on Jun. 11, 2003, the entire content of which is incorporated herein by reference.

FIELD OF THE INVENTION

This invention generally relates to a balloon pump driving apparatus applied for an intra-aortic balloon pump therapy, which is one of methods of aiding heart function.

BACKGROUND

An intra-aortic balloon pumping therapy is prescribed for patients who have suffered from deterioration of heart function such as heart failure. Hereinafter, the intra-aortic balloon pumping is referred to as the IABP. More particularly, a balloon catheter is inserted into the patient's aorta such as a descending aorta. A pressurized fluid is introduced or derived from a balloon pump driving system into the balloon catheter in time of the patient's heartbeat. A blood pressure in the patient's aorta can be increased or decreased in response to inflation of a balloon positioned in the aorta or deflation thereof. Therefore, the IABP is an auxiliary circulation apparatus for aiding the deteriorated heart function.

The inflation or deflation of the balloon should be operated relying upon the patient's heartbeat, thereby requiring a speedy response to the patient's heartbeat. In light of foregoing, recent developments have lead to an apparatus in which helium with high response is applied as the pressurized fluid flowing in the balloon catheter, improvements of a balloon pump driving system, and so on.

Japanese Patent Application Publication No. 5 (1993)-16870 discloses one of the above described recent developments. In general, a balloon pump driving system is provided with an isolator divided into an input chamber space and an output chamber space by a movable membrane. The output chamber space communicates with a balloon catheter via a common valve, while the input chamber space communicates with a positive pressure source or a negative pressure source. According to the invention described in the above-described reference, the common valve is closed when the balloon is deflating or while the balloon is under a deflated condition. In this case, the pressure in the output chamber space is increased and maintained at a positive pressure level. The balloon catheter is then set at the positive pressure level at a blast by opening the common valve at a predetermined timing. In the same manner, the common valve is closed when the balloon is inflating or while the balloon is under an inflated condition. In this case, the pressure in the output chamber space is decreased and maintained at a negative pressure level. The balloon catheter is then set at the negative pressure level at a blast by opening the common valve at a predetermined timing.

As described above, a following process can be prepared during a previous process by operatively associating the opening/closing control of the common valve and the pressure control in the output chamber space, thereby enabling to achieve a speedy pressure control.

In the meantime, Japanese Patent Laid-Open Publication No. 10 (1998)-328296 discloses an intra-aortic balloon pump having three isolators; a main isolator, a positive pressure isolator, and a negative pressure isolator. In a process for inflating a balloon, a positive pressure is applied to the balloon by communicating the main isolator and the positive pressure isolator with the balloon. Subsequently, the communication between the positive pressure isolator and the balloon is interrupted, while a predetermined gas is drawn out from the balloon side by the main isolator. Accordingly, an inflation pressure can be assured when the balloon is fully inflated. In the same manner, in a process for deflating the balloon, a negative pressure is applied to the balloon by communicating the main isolator and the negative pressure isolator with the balloon. Subsequently, the communication between the negative pressure isolator and the balloon is interrupted, while a predetermined gas is supplied to the balloon side by the main isolator. Accordingly, a deflation pressure can be assured when the balloon is fully deflated. As described above, in the process for inflating (for deflating) the balloon, a great volume of gas is drawn out of the balloon (is supplied to the balloon) by the main isolator and the positive (negative) pressure isolator. Therefore, a pressure differential can be maintained between the balloon side and the isolator side for a long period of time.

In a conventional system prior to the above-described systems, the pressure differential between the balloon side and the isolator side was decreased with a time-lapse. The balloon inflating speed (the balloon deflating speed) was slowed in response to the decrease of the pressure differential. However, according to the system described in the reference 2, the pressure differential can be maintained until the balloon is fully inflated (deflated). In this case, the pressure differential does not have to be decreased. Therefore, a time required for fully inflating (fully deflating) the balloon can be shortened.

SUMMARY OF THE INVENTION

According to a first aspect of the present invention, a balloon pumping method of inflating and deflating a balloon in a blood vessel at a predetermined timing includes the steps of setting a pressure in the balloon at a first pressure value, which is higher than a minimum pressure value for maintaining an inflated condition and is substantially equal to or lower than a maximum pressure value for maintaining the inflated condition, when the balloon is shifted from a deflated condition to an inflated condition, and decreasing the pressure in the balloon at a second pressure value, which is substantially equal to or higher than the minimum pressure value and lower than the first pressure value, after the balloon is estimated to have completely inflated at the first pressure value.

The minimum pressure value, at which the balloon can be maintained under the inflated condition, represents a bottom limiting value that the balloon can be inflated. The pressure in the vessel is an aortic pressure. Therefore, in order to inflate the balloon in the vessel, the balloon has to be maintained at a pressure higher than the aortic pressure. Therefore, the minimum pressure value can be higher than the aortic pressure. The aortic pressure fluctuates periodically and is different among patients. Therefore, the minimum pressure value cannot be always a fixed pressure value.

The maximum pressure value, at which the balloon can be maintained under the inflated condition, represents an upper limiting value that the balloon in the vessel does not deform and is not damaged. A load applied to a membrane forming the balloon fluctuates depending on a pressure differential between the aortic pressure and the balloon internal pressure. When the balloon internal pressure is too high relative to the aortic pressure, the membrane of the balloon may be excessively applied with the load, wherein the balloon membrane may be damaged, for example may be torn out. The maximum pressure value represents the upper Limiting value that the balloon is not damaged as described above.

According to a second aspect of the present invention, the balloon pumping method of inflating and deflating a balloon in a blood vessel at a predetermined timing includes the steps of setting a pressure in the balloon at a third pressure value, which is lower than a maximum pressure value for maintaining a deflated condition and is substantially equal to or higher than a minimum pressure value for maintaining the deflated condition, when the balloon is shifted from an inflated condition to the deflated condition; and increasing the pressure in the balloon to a fourth pressure value, which is substantially equal to or lower than the maximum pressure value and higher than the third pressure value, after the balloon is estimated to have completely deflated at the third pressure value.

The maximum pressure value, at which the balloon can be maintained under the deflated condition, represents an upper limiting value that the balloon can be deflated. The pressure in the vessel is an aortic pressure. Therefore, in order to deflate the balloon in the vessel, the balloon has to be maintained at a pressure lower than the aortic pressure. Therefore, the maximum pressure value can be lower than the aortic pressure. The aortic pressure fluctuates periodically and is different among patients. Therefore, the maximum pressure value cannot be always a fixed pressure value.

The minimum pressure value, at which the balloon can be maintained under the deflated condition, represents a bottom limiting value that the balloon in the vessel does not deform and is not damaged. A load applied to a membrane forming the balloon fluctuates depending on a pressure differential between the aortic pressure and the balloon internal pressure. When the balloon internal pressure is too low relative to the aortic pressure, the membrane of the balloon may be excessively applied with the load, wherein stress may be applied to a connecting portion between the balloon and the balloon catheter. Therefore, the durability may be deteriorated. The minimum pressure value represents the bottom limiting value that the balloon does not face the above-described states.

According to a third aspect of the present invention, a balloon pump driving apparatus connected to a balloon in a blood vessel and adapted to inflate and deflate the balloon at a predetermined timing by applying a predetermined pressure to the balloon includes inflation judging means for judging a timing for inflating the balloon based upon an inputted bio signal, first inflation pressure applying means for applying a first inflation pressure to the balloon at an appropriate timing judged by the inflation judging means, the first inflation pressure being higher than a minimum pressure value at which the balloon is maintained at an inflated condition, complete inflation estimating means for estimating whether the balloon has completely inflated by applying the first inflation pressure to the balloon by the first inflation pressure applying means, and second inflation pressure applying means for applying a second inflation pressure to the balloon when the complete inflation estimating means estimates that the balloon has completely inflated, the second inflation pressure being substantially equal to or higher than the minimum pressure value and lower than the first inflation pressure. Therefore, the pressure in the balloon is decreased.

In light of foregoing, according to a fourth aspect of the present invention, the balloon pump driving apparatus connected to a balloon inserted in to a blood vessel and adapted to inflate and deflate the balloon at a predetermined timing by applying a predetermined pressure to the balloon includes deflation judging means for judging a timing for deflating the balloon based upon an inputted bio signal, first deflation pressure applying means for applying a first deflation pressure to the balloon at an appropriate timing judged by the deflation judging means, the first deflation pressure being lower than a maximum pressure value at which the balloon is maintained at a deflated condition, complete deflation estimating means for estimating whether the balloon has completely deflated by applying the first deflation pressure by the first deflation pressure applying means, and second deflation pressure applying means for applying a second deflation pressure to the balloon when the complete deflation estimating means estimates that the balloon has completely deflated, the second deflation pressure being substantially equal to or lower than the maximum pressure value and higher than the first deflation pressure.

According to a fifth aspect of the present invention, the balloon pump driving apparatus includes a pressure accumulator connected to a balloon in a blood vessel and adapted to accumulate a pressure to be supplied to the balloon at a predetermined timing, a pressure control valve disposed between the pressure accumulator and the balloon, and means for controlling the pressure accumulated in the pressure accumulator and an open/closed condition of the pressure control valve. The means for controlling performs a first inflation pressure control for controlling the pressure accumulator so as to set the pressure accumulated in the pressure accumulator at a first inflation pressure, the first inflation pressure being higher than a minimum pressure value at which the balloon is maintained at an inflated condition, an inflation-time valve opening control for connecting the pressure accumulator with the balloon by opening the pressure control valve after accumulating the first inflation pressure in the pressure accumulator through the first inflation pressure control, a time judgment control for judging whether an opening period of the pressure control valve has reached a first predetermined period, an inflation-time intermediate valve closing control for closing the pressure control valve when the opening period of the pressure control valve is judged to be have reached the first predetermined period by the time judgment control, a pressure decrease control for decreasing the pressure accumulated in the pressure accumulator when the opening period of the pressure control valve is judged to have reached the predetermined period by the time judgment control, a complete inflation estimating control for estimating whether the balloon has completely inflated, an inflation-time intermediate valve opening control for opening the pressure control valve when the balloon is estimated to have completely inflated by the complete inflation estimating control, and an inflation-time valve closing control for closing the pressure control valve in a second predetermined time set at a time value at which the pressure in the balloon is expected to become higher than a minimum pressure value and lower than the first inflation pressure after opening the pressure control valve by the inflation-time intermediate valve opening control, the minimum pressure value at which the balloon is maintained under the inflated condition.

According to a seventh aspect of the present invention, the balloon pump driving apparatus includes a pressure accumulator connected to a balloon inserted in a blood vessel and adapted to accumulate a pressure to be supplied to the balloon at a predetermined timing, a pressure control valve disposed between the pressure accumulator and the balloon, and means for controlling the pressure accumulated in the pressure accumulator and an open/closed condition of the pressure control valve. The means for controlling performs a first deflation pressure control for controlling the pressure accumulator so as to set the pressure accumulated in the pressure accumulator at a first deflation pressure, the first deflation pressure being lower than a maximum pressure value at which the balloon is maintained at a deflated condition, a deflation-time valve opening control for connecting the pressure accumulator with the balloon by opening the pressure control valve after accumulating the first deflation pressure in the pressure accumulator through the first deflation pressure control, a complete deflation estimating control for estimating whether the balloon has completely deflated, a pressure increase control for increasing the pressure accumulated in the pressure accumulator when the balloon is estimated to have completely deflated by the complete deflation estimating control, a deflation pressure estimating control for estimating whether the pressure in the balloon has reached a predetermined pressure being lower than the maximum pressure and higher than the first deflation pressure, and a deflation valve closing control for closing the pressure control valve when the pressure in the balloon has reached the predetermined pressure by the deflation pressure estimating control.

According to an eighth aspect of the present invention, the balloon pump driving apparatus includes a pressure accumulator connected to a balloon inserted in a blood vessel and adapted to accumulate a pressure to be supplied to the balloon at a predetermined timing, a pressure control valve disposed between the pressure accumulator and the balloon, a first connecting passage connecting the auxiliary reservoir tank with the balloon, a first auxiliary switching valve disposed in the first connecting passage, and means for controlling the pressure accumulated in the pressure accumulator, an open/closed condition of the pressure control valve, and an open/closed condition of the first auxiliary switching valve. The means for controlling performs a first inflation pressure control for controlling the pressure accumulator so as to set the pressure accumulated in the pressure accumulator at a first inflation pressure, the first inflation pressure being higher than a minimum pressure value at which the balloon is maintained at an inflated condition, an inflation-time valve opening control for connecting the pressure accumulator with the balloon by opening the pressure control valve after accumulating the first inflation pressure in the pressure accumulator through the first inflation pressure control, a time judgment control for judging whether an opening period of the pressure control valve has reached a first predetermined period, an inflation-time intermediate valve closing control for closing the pressure control valve when the opening period of the pressure control valve is judged to be have reached the first predetermined period by the time judgment control, a pressure decrease control for decreasing the pressure accumulated in the pressure accumulator when the pressure control valve is closed by the inflation-time intermediate valve closing control, a complete inflation estimating control for estimating whether the balloon has completely inflated, an inflation-time intermediate valve opening control for setting the pressure in the balloon higher than the minimum pressure and lower than the first inflation pressure by establishing a communication between the auxiliary reservoir tank and the balloon by opening the first auxiliary switching valve when the balloon is estimated to have completely inflated by the complete inflation estimating control, the pressure in the auxiliary reservoir tank having been set at a second inflation pressure, an inflation-time valve closing control for interrupting the communication between the auxiliary reservoir tank and the balloon by closing the first auxiliary switching valve in a predetermined period of time after opening the first auxiliary switching valve by the inflation-time intermediate valve opening control, an auxiliary reservoir pressure setting control for setting the pressure in the auxiliary reservoir tank at a predetermined pressure.

According to a ninth aspect of the present invention, the balloon pump driving apparatus includes a pressure accumulator connected to a balloon in a blood vessel and adapted to accumulate a pressure to be supplied to the balloon at a predetermined timing, a pressure control valve disposed between the pressure accumulator and the balloon, a first connecting passage connecting the auxiliary reservoir and the balloon, a first auxiliary switching valve disposed in the first connecting passage, and means for controlling the pressure accumulated in the pressure accumulator, an open/closed condition of the pressure control valve, and an open/closed condition of the first auxiliary switching valve. The means for controlling performs a first deflation pressure control for controlling the pressure accumulator so as to set the pressure accumulated in the pressure accumulator at a first deflation pressure, the first deflation pressure being lower than a maximum pressure value at which the balloon is maintained at a deflated condition, a deflation-time valve opening control for connecting the pressure accumulator with the balloon by opening the pressure control valve after accumulating the first deflation pressure in the pressure accumulator through the first deflation pressure control, a complete deflation estimating control for estimating whether the balloon has completely deflated, a deflation-time intermediate valve opening control for setting the pressure in the balloon to be lower than the maximum pressure and higher than the first deflation pressure by establishing a communication between the auxiliary reservoir tank and the balloon by opening the first auxiliary switching valve while the pressure control valve is opened when the balloon is estimated to have completely deflated by the complete deflation estimate control, the pressure in the auxiliary reservoir tank having been set at a second deflation pressure, a deflation-time valve closing control for interrupting the communication between the pressure accumulator and the balloon by closing the pressure control valve in a predetermined period of time after opening the first auxiliary switching valve by the deflation-time intermediate valve opening control, a pressure increase control for increasing the pressure accumulated in the pressure accumulator after closing the pressure control valve by the deflation-time valve closing control, a deflation-time intermediate valve closing control for interrupting the communication between the auxiliary reservoir tank and the balloon by closing the first auxiliary switching valve substantially at a same time as the closing operation of the pressure control valve by the deflation-lime valve closing control or after the closing operation thereof, and an auxiliary reservoir pressure setting control for setting the pressure in the auxiliary reservoir tank at a predetermined pressure.

According to a tenth aspect of the present invention, the balloon pump driving apparatus includes the pressure accumulator having an isolator housing of which inside is a hollow, isolator means having a movable membrane disposed in the isolator housing, the inside of the isolator housing divided into an output chamber and an input chamber by the movable membrane, the output chamber connected to the balloon via the pressure control valve; and movable membrane driving means for displacing the movable membrane in the isolator housing.

In this case, the pressure accumulator can be configured with a simple structure.

According to an eleventh aspect of the present invention, a fluid-type pump displaces the movable membrane. Generally, the movable membrane is displaced by a compressor as a non-limiting example. However, according to the ninth aspect of the present invention, the size of the isolator can be downsized. Further, the pressure accumulated by the isolator means continuously varies by adjusting the fluid amount in the fluid-type pump.

BRIEF DESCRIPTION OF THE DRAWINGS

The foregoing and additional features and characteristics of the present invention will become more apparent from the following detailed description considered with reference to the accompanying drawings, wherein.

DETAILED DESCRIPTION

Figure 1:
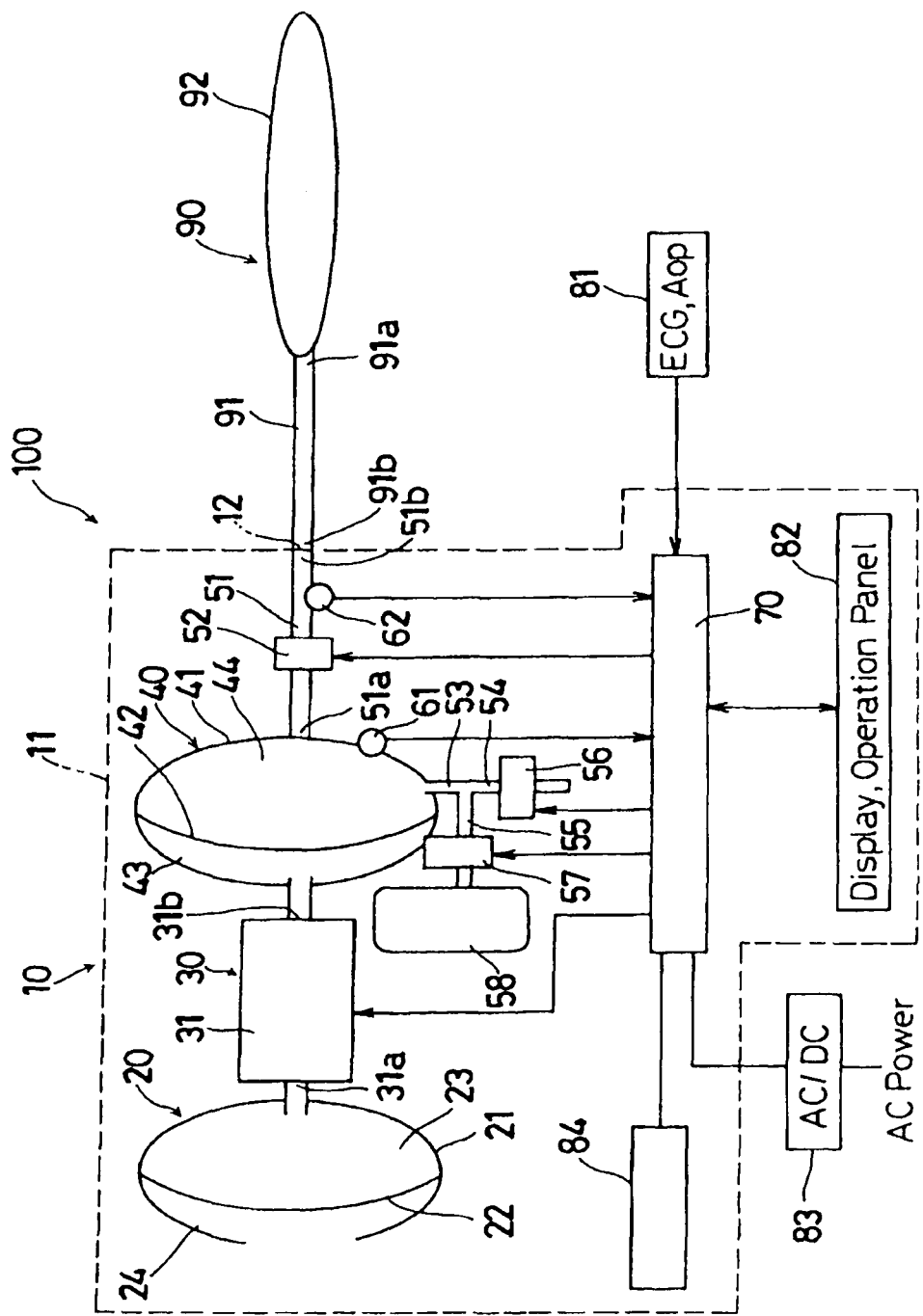
FIG. 1 is a schematic view illustrating a balloon pumping system according to a first embodiment of the present invention.

As illustrated in FIG. 1, a balloon pumping system 100 according to a first embodiment of the present invention includes a balloon catheter 90 and a balloon pump driving apparatus 10. The balloon catheter 90 includes a catheter 91 and a balloon 92. The catheter 91 is a long tube with a lumen and is made of a material possessing certain degree of flexibility. The balloon 92 is equipped at a distal end 91a of the catheter 91, i.e. is equipped at an end of the catheter 91 that is away from the balloon pump driving apparatus 10, while the balloon pump driving apparatus 10 is equipped at a proximal end 91b of the catheter 91, i.e. is equipped at an end of the catheter 91 opposite to the distal end 91a.

The balloon pump driving apparatus 10 is provided with an outer shell of an apparatus housing 11 which houses an oil reservoir 20, an oil pump 30, and an isolator 40. The oil pump 30 includes a pump housing 31 having a first input-output port 31a (a first I/O port) and a second input-output port 31b (a second I/O port). The pump housing 31 includes a pumping chamber (not illustrated) having an impeller blade, and a driving power source (not illustrated) such as a motor that is connected to the impeller blade. A rotational shaft of the motor can be rotated in normal and reverse directions. The first I/O port 31a is connected to the oil reservoir 20, while the second I/O port 31b is connected to the isolator 40.

The oil reservoir 20 includes a reservoir housing 21 and a reservoir diaphragm (i.e., a movable membrane) 22 disposed in the reservoir housing 21. The reservoir housing 21 is divided into an oil chamber 23 and an air-releasing chamber 24 by the reservoir diaphragm 22. As illustrated in FIG. 1, the oil chamber 23 communicates with the first I/O port 31a, while the air-releasing chamber 24 communicates with an air such that an internal pressure in the air-releasing chamber 24 is always maintained at an atmospheric pressure level.

The isolator 40 is referred to as a volume limiting device (VLD) and corresponds to a pressure accumulator. The isolator 40 includes an isolator housing 41 and an isolator diaphragm 42 disposed in the isolator housing 41. The isolator housing 41 is divided into two chambers by the isolator diaphragm 42; one is an input chamber 43 and the other one is an output chamber 44. As illustrated in FIG. 1, the input chamber 43 communicates with the second I/O port 31b of the oil pump 30, while the output chamber 44 communicates with a one end 51a of an output conduit 51. The other end 51b of the output conduit 51 communicates with an output port 12 formed at a surface of the apparatus housing 11. The output port 12 is connected to the proximate end 91b of the catheter 91, such that the balloon catheter 90 communicates with the output conduit 51.

A pressure control valve 52 referred to as a common valve is disposed in the output conduit 51. A flow passage area of the pressure control valve 52 under an open condition is designed to be larger than the one of a normal switching valve. Therefore, pressure loss can be effectively prevented, which may be caused upon opening the pressure control valve 52.

As illustrated in FIG. 1, the output chamber 44 further communicates with a helium gas supply-drain conduit 53 which branches to a gas drain conduit 54 and a gas supply conduit 55. There is a drain switching valve 56 disposed in the gas drain conduit 54. An opening end of the gas drain conduit 54 communicates with an air. In the meantime, there is a supply switching valve 57 disposed in the gas supply conduit 55. An end of the gas supply conduit 55, which is different from a branched end thereof, is connected to a helium gas tank 58. According to the first embodiment of the present invention, the gas drain conduit 54 and the gas supply conduit 55 are merged in midstream to communicate with the output chamber 44. Alternatively, the gas drain conduit 54 and the gas supply conduit 55 can communicate with the output chamber 44 independently.

A first pressure sensor 61 is equipped in the output chamber 44 of the isolator 40 so as to detect the pressure in the output chamber 44. A second pressure sensor 62 is equipped at a downstream side of the pressure control valve 52 at the output conduit 51, i.e., at a side near the balloon catheter 90. A portion equipped with the second pressure sensor 62 at the output conduit 51 always communicates with the balloon catheter 90 via the output port 12. Therefore, the second pressure sensor 62 can detect a pressure applied to the balloon 92.

The balloon pump driving apparatus 10 is further provided with a controller 70. The controller 70 is electrically connected to a driving means of the oil pump 30, the supply switching valve 57, the drain switching valve 56, the pressure control valve 52, the first pressure sensor 61, and the second pressure sensor 62. The controller 70 is further electrically connected to a biological signal output device 81 and a display-operating panel 82. The biological signal output device 81 outputs an electrocardiographic (ECG) signal and/or an aortic pressure (Aop) signal. The controller 70 is transmitted with requisite information such as the ECG signal and/or the Aop signal outputted from the biological signal output unit 81, the pressure information detected by the first and second pressure sensors 61 and 62, and so on. The controller 70 then outputs a drive control signal to the driving means of the oil pump 30, and outputs switching signals to the supply switching valve 57, the drain switching valve 56, and the pressure control valve 52, respectively. The controller 70 is still further connected to an AC/DC adapter 83 connected to a normal alternator and a battery 84 as an auxiliary power source.

The oil chamber 23 of the oil reservoir 20 has been charged with oil. This oil is supplied to or drained from the input chamber 43 of the isolator 40 by the oil pump 30. That is, a primary space defined by the oil chamber 23 of the oil reservoir 20, the pumping chamber of the oil pump 30, and the input chamber 43 of the isolator 43 can be charged with the oil. Any type of oil can be applied. However, it is preferable to apply silicon oil in light of safety level and response.

The output chamber 44 has been charged with helium gas. The helium gas is supplied from the helium gas tank 58 to the output chamber 44 when the supply switching valve 57 is opened. The amount of the helium gas charging the output chamber 44 can be determined based upon a value of the pressure detected by the first pressure sensor 61 at a predetermined timing while the balloon pump driving apparatus 10 has been normally operated. When the amount of the helium gas is judged to have not been sufficiently supplied to the output chamber 44, the supply switching valve 57 is opened so as to supply more helium gas to the output chamber 44.

Next, operation of the balloon pumping system 100 will be explained hereinbelow with reference to FIGS. 2, 3A, and 3B. As explained by a timing chart illustrated in FIG. 2, a sequential line graph denoted with a solid line explains bow a pressure Pi in the output chamber 44 detected by the first pressure sensor 61 transits, while a sequential line graph denoted with a dotted line explains how a pressure Pb applied to the balloon 92 and detected by the second pressure sensor 62 transits. The pressure Pb substantially corresponds to a pressure in the balloon 92. The balloon pumping system 100 repeats inflation and deflation of the balloon 92, such that there is no clear definition of a starting point. Therefore, the following explanation will be initiated from a point Q in FIG. 2, i.e., from a condition where the pressure control valve 52 is closed and the balloon 92 has deflated with the applied pressure Pb at a second deflation pressure P4.

Figure 3A:
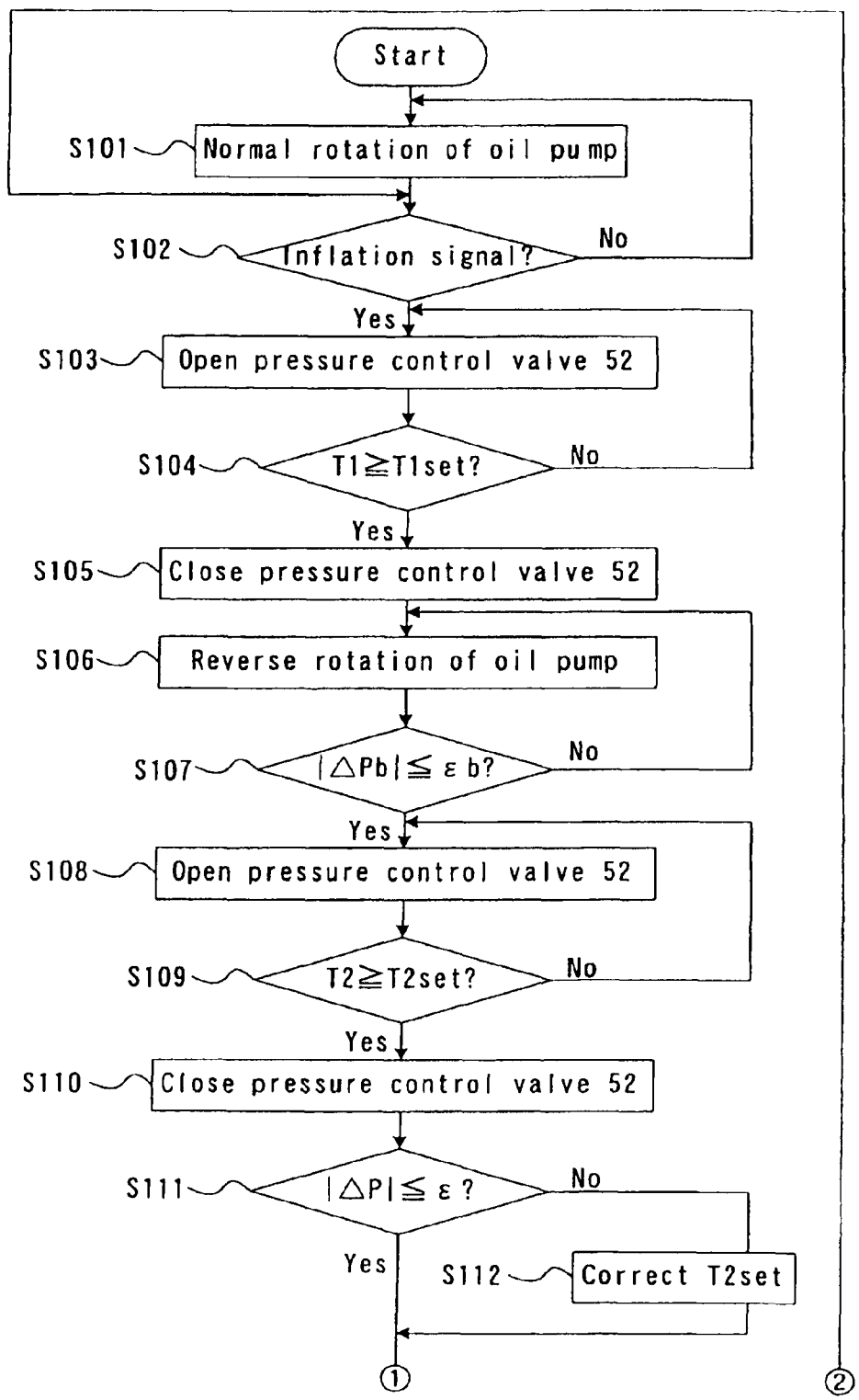
FIGS. 3A and 3B are a main flowchart of a controller for inflating and deflating the balloon by the balloon pumping system illustrated in FIG. 1.

Under the above-described condition, the oil pump 30 is driven for rotation in the normal direction as explained at step S101 in FIG. 3A. In response to the normal rotation of the oil pump 30, the oil in the oil reservoir 20 is introduced to the oil pump 30 through the first I/O port 31a. The oil is then drained to the input chamber 43 of the isolator 40 through the second I/O port 31b. In this case, the isolator diaphragm 42 moves and extends in a right direction in FIG. 1. In response to the extension of the isolator diaphragm 42, the volume of the output chamber 44 is decreased such that the pressure Pi of the output chamber 44 is detected at a higher pressure value by the first pressure sensor 61. When the pressure Pi in the output chamber 44 reaches a first inflation pressure P1, the rotational speed of the oil pump 30 is slowed down so as not to increase the pressure Pi any more. The amount of oil discharged from the oil pump 30 to the isolator 40 can be balanced with the amount of oil flowing back from the isolator 40 to the oil pump 30. Accordingly, the pressure Pi in the output chamber 44 can be maintained at the first inflation pressure P1 (a first inflation pressure control). The first inflation pressure P1 is far higher than a pressure required for inflating the balloon 92.

At step S102, the controller 70 judges the presence or absence of an inflation signal for the balloon 92 (inflation judging means). The controller 70 computes timing for inflating the balloon 92, which is appropriate for a body condition of a patient, based upon the ECG signal and/or the Aop signal. The controller 70 outputs the inflation signal in response to the computed timing. When the controller 70 judges that the inflation signal has not been outputted, the program returns to step S101. When the controller 70 judges that the inflation signal has been outputted, the program proceeds to step S103. An explanation of a method of computing the appropriate inflation timing will be omitted herein.

When the inflation signal is outputted at step S102, the controller 70 recognizes that the balloon 92 is under an inflating period, i.e., the balloon 92 is shifting from a deflation condition to an inflation condition. At step S103, the controller 70 outputs a command signal for opening the pressure control valve 52 (an inflation-time valve opening control) in response to the opening operation of the pressure control valve 52, the output chamber 44 of the isolator 40 communicates with the balloon 92 such that the first inflation pressure P1 in the output chamber 44 is applied to the balloon 92. In this case, the pressure Pb is rapidly increased up to a pressure P1' from the second deflation pressure P4.

As described above, the output chamber 44 has been charged with the first inflation pressure P1 higher than the pressure required for inflating the balloon 92 until a timing immediately before the pressure control valve 52 is opened. Therefore, once the pressure control valve 52 is opened, the helium gas in the output chamber 44 at a blast flows into the balloon 92. Therefore, according to the first embodiment of the present invention, the balloon 92 can be inflated much faster than the conventional method.

The program then proceeds to step S104 after opening the pressure control valve 52, at which the controller 70 judges whether the pressure control valve 52 has opened for a set period T1set (i.e., a first predetermined period), i.e., judges whether an opening period T1 of the pressure control valve 52 is substantially equal to or greater than the set period T1set (a T1 judging control). When the controller 70 judges that the opening period T1 has not reached the set period T1set, the program returns to step S103. In the meantime, when the controller 70 judges that the opening period T1 has reached the set period T1set, the program proceeds to step S105. The set period T1set is designed as Deeded based upon a material of the balloon 92, the information of the signal outputted from the biological signal output device 81, and so on. However, it is preferable that the set period T1set be designed at an expected period of time for supplying the sufficient amount of helium gas required for completely inflating the balloon 92 at a predetermined pressure level.

At step S105, the controller 70 closes the pressure control valve 52 (an inflation-time intermediate valve closing control). The communication between the output chamber 44 and the balloon 92 is interrupted in response to the closing operation of the pressure control valve 52. The program then proceeds to step S106.

At step S106, the controller 70 drives the oil pump 30 for rotation in a reverse direction. The oil in the input chamber 43 of the isolator 40 is then sucked into the oil pump 30 through the second I/O port 31b. The oil in the oil pump 30 is then drained into the oil chamber 23 of the oil reservoir 20 through the first I/O port 31a. Therefore, the isolator diaphragm 42 then moves in a left direction in FIG. 1. The volume of the output chamber 44 is increased corresponding to the movement of the diaphragm 42 such that the pressure Pi in the output chamber 44 is decreased as explained in FIG. 2 (a pressure decrease control).

A pressure change rate (with time) of the pressure value Pb detected by the second pressure sensor 62 is denoted with a pressure change rate ÄPb with time. At step S107, the controller 70 judges whether the pressure change rate ÄPb is zero or within a predetermined range åb, i.e., judges whether the balloon 92 has completely inflated (a complete inflation estimating control). The balloon 92 has not completely inflated immediately after closing the pressure control valve 52 at step S105 such that the balloon 92 is inflating even after the valve closing operation. The helium gas flows from the output chamber 44 to the balloon 92 in response to this balloon inflation. Therefore, the pressure Pb applied to the balloon 92 is decreased. However, when the balloon 92 approaches the completely inflated condition, the amount of helium gas flowing into the balloon 92 is decreased, wherein the decreasing amount of the pressure Pb becomes less, i.e., the pressure change rate ÄPb with time becomes slow. When the balloon 92 is completely inflated, no more helium gas flow into the balloon 92. In this case, the decrease of the pressure Pb is stopped, and the pressure Pb is maintained at a flat pressure level. As described above, the balloon 92 can be judged whether it has completely inflated, based upon the pressure change rate ÄPb.

Figure 2:
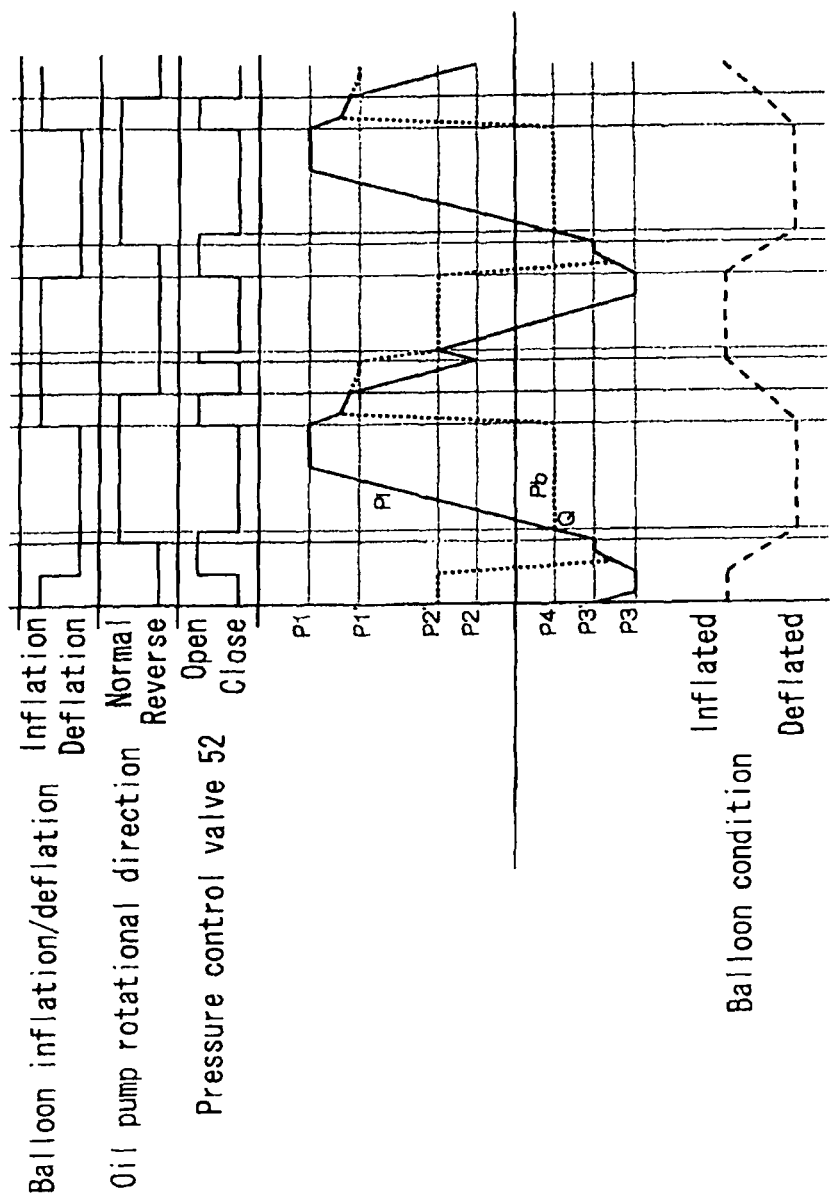
FIG. 2 is a timing chart for explaining transitions of a timing for inflating and deflating a balloon, an inflated and deflated condition of the balloon, a rotational direction of an oil pump, a timing for switching a pressure control valve, a pressure in an output chamber, and a pressure applied to the balloon according to the first embodiment of the present invention.
Figure 3B:
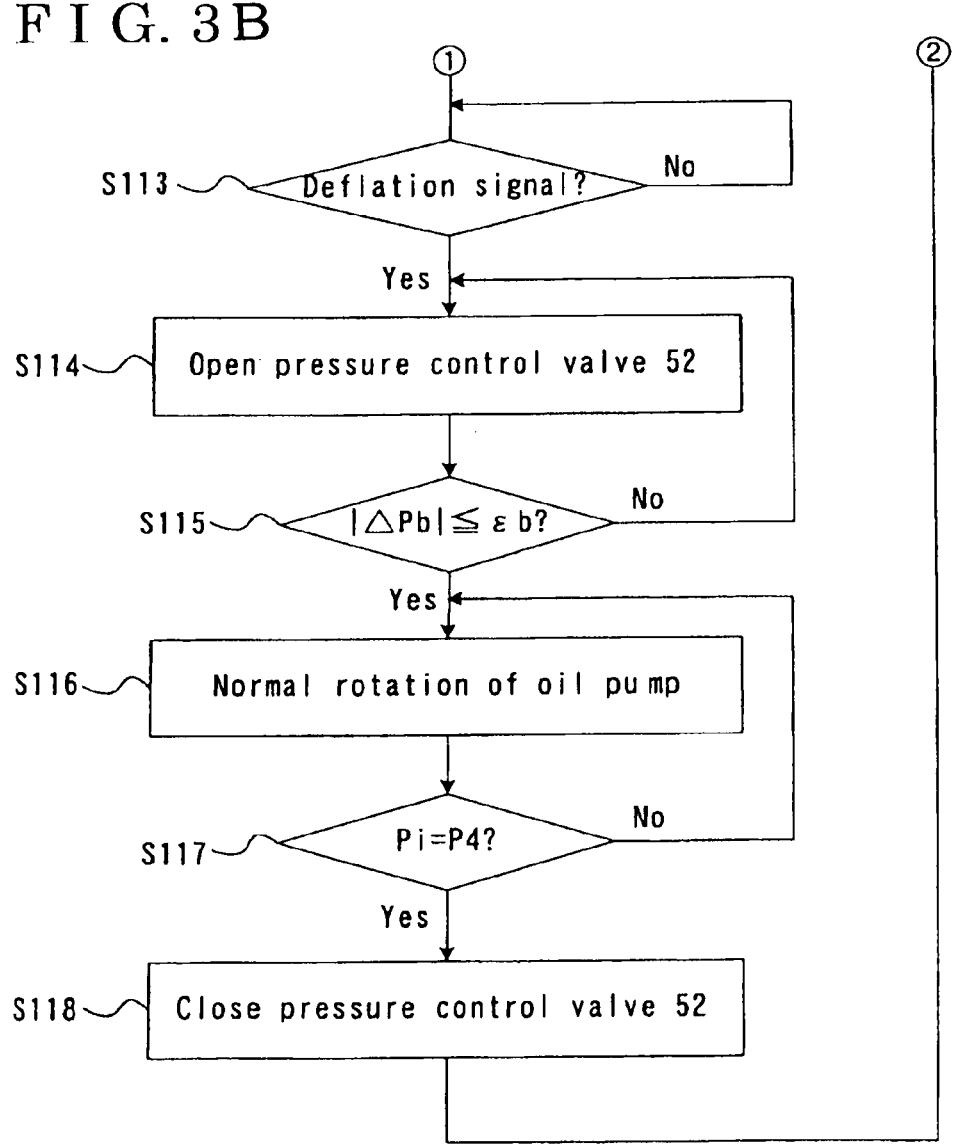

As explained in FIG. 2, according to the first embodiment of the present invention, the pressure change rate ÄPb becomes approximately zero during the inflating period. In this case, the pressure Pb has reached the pressure P1'. The pressure P1' is higher than the minimum pressure value capable of maintaining the balloon 92 at the inflated condition, and is lower than the maximum pressure value capable of maintaining the balloon 92 at the inflated condition. On the other hand, according to a conventional balloon pump driving apparatus, the pressure in the balloon is set around the minimum pressure level capable of maintaining the balloon under the inflated condition when the balloon is completely inflated. Comparing the balloon pump driving apparatus 10 with this type of conventional balloon pump driving apparatus, the balloon 92 can be inflated faster because the balloon 92 has been applied with the pressure P1' higher than the conventional applied pressure even when the balloon 92 has completely inflated. It is preferable that the pressure P1' be set at a pressure value proximal to the maximum pressure at which the balloon 92 is maintained at the inflated condition. That is, it is preferable that the pressure P1' be set at a pressure value as high as possible within an allowable pressure range. By setting the pressure P1' at a relatively high value, the balloon 92 can be effectively inflated at a much faster inflating speed.

When the pressure change rate ÄPb is judged to have been substantially equal to zero or to be within the range åb, the program proceeds to step S108, wherein the pressure control valve 52 is opened again (the inflation-time intermediate valve opening control). The oil pump 30 has rotated in the reverse direction after the closing operation of the pressure control valve 52 at step S105, such that the pressure Pi in the output chamber 44 of the isolator 40 has been decreased down to the second inflation pressure P2. Therefore, in response to the opening operation of the pressure control valve 52, the output chamber 44 set at a decreased pressure level communicates with the balloon 92 set at a high pressure level, wherein the helium gas in the balloon 92 is drawn back to the output chamber 44. Therefore, the pressure level in the balloon 92 is decreased.

The program then proceeds to step S109 after opening the pressure control valve 52 at step S108, at which the controller 70 judges whether the pressure control valve 52 has opened for a set period T2set (i.e., a second predetermined time), i.e., judges whether an opening period T2 of the pressure control valve 52 is substantially equal to or greater than the set period T2set. When the controller 70 judges that the opening period T2 has not reached the set period T2set, the program returns to step S108. When the controller 70 judges that the opening period T2 has reached the set period set, the program proceeds to step S110.

At step S110, the controller 70 closes the pressure control valve 52 (an inflation-time valve closing control). The communication between the output chamber 44 and the balloon 92 is interrupted in response to the closing operation of the pressure control valve 52. The balloon 92 is then maintained under the inflated condition at an applied pressure P2'. The program then proceeds to step S111. As explained in FIG. 2, the applied pressure Pb is constantly maintained at the pressure P2' while the balloon 92 has been under the inflated condition. The balloon 92 can be hence expected to be maintained at this pressure P2' level. It is preferable that the pressure P2' be set at a value proximate to the minimum pressure value capable of maintaining the balloon 92 under the inflated condition. That is, it is preferable that the pressure P2' be set at a pressure value as low as possible within an allowable pressure range. By setting the pressure P2' at a low value as described above, a pressure differential can be minimized when the balloon 92 is next shifted form the inflated condition to the deflated condition.

An appropriate pressure Pb to be applied to the balloon 92 is denoted with a set pressure Pset. A pressure differential between the set pressure Pset and the actual pressure Pb is denoted with an absolute pressure value $\overline{AP}$. At step S111, the controller 70 judges whether the absolute pressure value $\overline{AP}$ is substantially zero or within a predetermined range å. When the controller 70 judges that the absolute pressure value ÄP is substantially zero, or the absolute pressure value ÄP is substantially equal to or smaller than the predetermined range å, the program proceeds to step S113. On the other hand, when the controller 70 judges that the absolute value ÄP is not substantially zero, or the absolute pressure value ÄP is substantially equal to or greater than the predetermined range å, the program proceeds to step S112, at which the set period T2set is corrected (a correcting control).

The set period T2set is designed beforehand through experimentations. More particularly, the set period T1set is designed by measuring a transit time of the pressure Pb from the second inflation pressure P2 to the set pressure Pset upon the opening operation of the pressure control valve 52 at step S108. The set period T2set is set at a value obtained through the experimentation. However, the set period T2set may fluctuate due to the condition of the patient or a dimension of the balloon 92. Therefore, the pressure Pb does not always reach the pressure Pset in the set period T2set. In this case, the set period T2set is required to be corrected. The detailed description of the method of correcting the set period T2set will be omitted herein. For example, when the value ÄP at step S111 is a positive value, the set period T2set is corrected to be longer corresponding to the positive value ÄP. On the other hand, when the value ÄP at step S1 is a negative value, the set period T2set is corrected to be shorter corresponding to the negative value $\overline{AP}$. The program then proceeds to step S113.

The oil pump 30 has still rotated in the reverse direction even after closing the pressure control valve 52 at step S110. In this case, the isolator diaphragm 42 has expanded in the left direction in FIG. 1, wherein the volume of the output chamber 44 is increased. In this case, the pressure Pi in the output chamber 44 is further decreased down to a first deflation pressure P3. The rotational speed of the oil pump 30 in the reverse direction is slowed down to prevent occurrence of a further pressure decrease in the output chamber 44. The amount of oil introduced from the isolator 40 to the oil pump 30 is substantially balanced with the amount of oil flown back to the isolator 40 from the oil pump 30. Therefore, the pressure Pi in the output chamber 44 can be maintained at the first deflation pressure P3 (a first deflation pressure control). The first deflation pressure P3 is designed to be far lower than a pressure required for deflating the balloon 92.

At step S113, the controller 70 judges the presence or absence of a deflation signal of the balloon 92 (a deflation judging means). In the same manner as the judgment of the presence of absence of the inflation signal, the controller 70 computes timing for deflating the balloon 92, which is appropriate for the body condition of the patient, based upon the ECG signal and/or the Aop signal. The controller 70 outputs the deflation signal in response to the computed timing. When the controller 70 judges that the deflation signal has not been outputted, the program returns to step S113. When the controller 70 judges that the deflation signal has been outputted, the program proceeds to step S114.

When the deflation signal is outputted at step S113, the controller 70 recognizes that the balloon 92 is under the deflating period, i.e., the balloon 92 is shifted from the inflation condition to the deflation condition. At step S114, the controller 70 outputs a command signal for opening the pressure control valve 52 (a deflation-time valve opening control). In response to the opening operation of the pressure control valve 52, the output chamber 44 of the isolator 40 communicates with the balloon 92. The pressure Pb at the second inflation pressure P2' is higher than the pressure P3 in the output chamber 44. Therefore, the helium gas in the balloon 92 is drawn to the output chamber 44. In this case, the pressure Pb of the balloon 92 is suddenly decreased from the second inflation pressure P2' to a pressure P3'. The output chamber 44 has been charged with the first inflation pressure P3 until timing immediately before the opening operation of the pressure control valve 52. Therefore, in response to the opening operation of the pressure control valve 52, the helium gas at a blast flows from the balloon 92 to the output chamber 44. Therefore, according to the first embodiment of the present invention, the deflation of the balloon 92 can be performed faster than the conventional balloon pumping system.

After opening the pressure control valve 52 at step S114, the program proceeds to step S115, at which the controller 70 judges whether the pressure change rate ÄPb of the pressure Pb for the balloon 92 is substantially zero or within the predetermined range åb, i.e., judges whether the balloon 92 has completely deflated (a complete deflation estimating control). The balloon 92 has not completely deflated immediately after opening the pressure control valve 52 at step S114 such that the balloon 92 is deflating even after the valve opening operation. The helium gas flows from the balloon 92 to the output chamber 44 in response to this balloon deflation. Therefore, the pressure Pb applied to the balloon 92 is increased. However, when the balloon 92 approaches the completely deflated condition, the amount of helium gas flowing from the balloon 92 is decreased, wherein the increasing amount of the pressure Pb becomes less, i.e., the pressure change rate $\overline{APb}$ with time becomes slow. When the balloon 92 is completely deflated, no more helium gas flows from the balloon 92. In this case, the increase of the pressure Pb is stopped, and the pressure Pb is maintained at a flat pressure level. As described above, the balloon 92 can be judged whether it has completely deflated, based upon the pressure change rate $\overline{APb}$.

As explained in FIG. 2, according to the first embodiment of the present invention, the pressure change rate ÄPb becomes approximately zero during the deflating period. In this case, the pressure Pb has reached the pressure P3'. The pressure P3' is lower than the maximum pressure value capable of maintaining the balloon 92 at the deflated condition, and is higher than the minimum pressure value capable of maintaining the balloon 92 at the deflated condition. On the other hand, according to a conventional balloon pump driving apparatus, the pressure in the balloon is set around the maximum pressure level capable of maintaining the balloon under the deflated condition when the balloon is completely deflated. Comparing the balloon pump driving apparatus 10 with this type of conventional balloon pump driving apparatus, the balloon 92 can be deflated faster because the balloon 92 has been applied with the pressure P3' lower than the conventional applied pressure even when the balloon 92 has completely deflated. It is preferable that the pressure P3' be set at a pressure value proximate to the minimum pressure value at which the balloon 92 is maintained at the deflated condition. That is, it is preferable that the pressure P3' be set at a pressure value as low as possible within an allowable pressure range. By setting the pressure P3' at a relatively low value as described above, the balloon 92 can be effectively deflated at a much faster deflating speed.

When the pressure change rate $\overline{APb}$ is judged to have been substantially equal to zero or to be within the range åb, the program proceeds to step S116, wherein the oil pump 30 is driven for rotation in the normal direction. The oil in the oil reservoir 20 is suck into the oil pump 30. The oil in the oil pump 30 is drained to the input chamber 43 of the isolator 30. In this case, the isolator diaphragm 42 expands in the right direction in FIG. 1. In response to the movement of the isolator diaphragm 42, the volume of the output chamber 44 is decreased, wherein the pressure Pi in the output chamber 44 is increased (a pressure increase control).

At step S117, the controller 70 judges whether the pressure Pi in the output chamber 44 detected by the first pressure sensor 61 is substantially equal to the second deflation pressure P4 (a deflation pressure estimating control). At this point, the pressure control valve 52 is at the open condition. That is, the pressure Pi in the output chamber 44 can be substantially equal to the pressure Pb applied to the balloon 92. When the controller 70 judges that the pressure Pi in the output chamber 44 is not substantially equal to the pressure P4, the program returns to step S116. When the controller 70 judges that the pressure Pi in the output chamber 44 is substantially equal to the pressure P4, the program proceeds to step S118, at which the pressure control valve 52 is closed (a deflation-time valve closing control). The communication between the output chamber 44 and the balloon 92 is interrupted. The pressure Pb applied to the balloon 92 is maintained at the pressure P4, and the balloon 92 is maintained under the deflated condition. The program then returns to step S102 so as to output the inflation signal for the next inflation. According to the first embodiment of the present invention, the balloon 92 can be effectively inflated and deflated at an appropriate timing by repeatedly performing the above-described procedure.

As described above, a balloon pumping method of inflating and deflating the balloon 92 in a vessel at a predetermined timing includes the step of setting the pressure in the balloon at the pressure P1' (i.e., a first pressure value), which is higher than the minimum pressure value and is substantially equal to or lower than the maximum pressure value, when the balloon 92 is shifted from the deflated condition to the inflated condition. The balloon 92 can be maintained under the inflated condition when the pressure in the balloon 92 is between the minimum pressure value and the maximum pressure value. The balloon pumping method further includes the step of decreasing the pressure in the balloon 92 to the pressure P2' (i.e., a second pressure value), which is substantially equal to or higher than the minimum pressure value and lower than the first pressure value, when the balloon 92 is estimated to have completely inflated at the first pressure value.

Taking the balloon pumping apparatus disclosed in the reference 2 as an example, when the balloon is inflating, the balloon is applied with a pressure higher than the minimum pressure at which the balloon can be maintained at the inflated condition. As the balloon is approaching the completely inflated condition, the applied pressure is reduced. When the balloon was shifted to the completely inflated condition, the pressure in the balloon is maintained at the minimum pressure at which the balloon can be maintained at the inflated condition. In this case, the pressure differential can be minimized when the balloon is shifted to the deflated condition from the inflated condition. Some of the main reasons of setting the pressure in the balloon at the minimum pressure are in order to ensure quick response for deflating the balloon, to prevent the balloon from unnecessary deformation, which may occur by applying excessive pressure to the balloon.

On the other hand, according to the first embodiment of the present invention, the pressure in the balloon 92 is set at the pressure P1', which is higher than the minimum pressure at which the balloon 92 can be maintained at the inflated condition and substantially equal to and lower than the maximum pressure value. The pressure in the balloon 92 is maintained at the pressure higher than the minimum pressure even when the balloon 92 has completely inflated. Therefore, the balloon inflation can be performed at a faster inflating speed corresponding to the pressure in the balloon 92. If the balloon pressure is maintained at this pressure level even when the balloon is shifted from the inflated condition to the deflated condition, the pressure differential may be unnecessarily increased. In this case, it may be difficult to deflate the balloon 92 at a quick deflating speed. In light of foregoing, the pressure in the balloon 92 is reduced to the pressure P2' when the balloon 92 is estimated to have completely inflated at the pressure P1'. The pressure P2' is substantially equal to or higher than the minimum pressure and is lower than the pressure P1'. Accordingly, the pressure differential upon deflating the balloon 92 can be decreased. Therefore, the balloon deflation can be performed quickly.

As described above, according to the first embodiment of the present invention, the balloon inflating/deflating response can be effectively improved by assuring the quick inflating response and the quick deflating response for the next balloon deflation.

The pressure P1' can be set at any pressure level between the minimum pressure value at which the balloon 92 can be maintained at the inflated condition and the maximum pressure value at which the balloon 92 can be maintained at the inflated condition. However, the higher the pressure P1' is set, the more quickly the balloon 92 can be inflated. Therefore, it is preferable that the pressure P1' be proximate to the maximum pressure value.

As far as the pressure P2' is lower than the pressure P1', the pressure P2' can be set at any pressure level between the minimum pressure value at which the balloon 92 can be maintained at the inflated condition and at the maximum pressure value at which the balloon 92 can be maintained at the inflated condition. However, the lower the pressure P2' is set, the pressure differential upon the next balloon inflation can be reduced. Therefore, it is preferable that the pressure P2' be proximate to the minimum pressure value, wherein the deflating response can be quickly performed at the next deflation.

The pumping method of inflating and deflating the balloon 92 in a vessel at the predetermined timing includes the step of setting the pressure in the balloon 92 at the pressure P3' (i.e., a third pressure value), which is lower than the maximum pressure value and is substantially equal to or higher than the minimum pressure value, when the balloon 92 is shifted from the inflated condition to the deflated condition. The balloon 92 can be maintained under the deflated condition when the pressure in the balloon 92 is between the minimum pressure value and the maximum pressure value. The balloon pumping method further includes the step of increasing the pressure in the balloon 92 to the pressure P4 (i.e., a fourth pressure value), which is substantially equal to or lower than the maximum pressure value and higher than the pressure P3', when the balloon 92 is estimated to have completely deflated at the third pressure value.

Taking a conventional balloon pumping apparatus as an example, when the balloon is inflating, the balloon is applied with a pressure lower than the maximum pressure at which the balloon can be maintained at the deflated condition. As the balloon is approaching the completely deflated condition, the applied pressure is increased. When the balloon was shifted to the completely deflated condition, the pressure in the balloon is maintained at the maximum pressure at which the balloon can be maintained at the deflated condition. In this case, the pressure differential can be minimized when the balloon is shifted to the inflated condition from the deflated condition. Some of the main reasons of setting the pressure in the balloon at the maximum pressure level are in order to ensure quick response for inflating the balloon, in order to prevent the balloon from unnecessary deformation, which may occur by applying excessive pressure to the balloon, and so on.

On the other hand, according to the first embodiment of the present invention, the pressure in the balloon 92 is set at the pressure P3', which is lower than the maximum pressure at which the balloon 92 can be maintained at the deflated condition, and is substantially equal to and higher than the minimum pressure value. The pressure in the balloon 92 is maintained at a pressure lower than the maximum pressure even when the balloon 92 has completely deflated. Therefore, the balloon deflation can be performed at a faster deflating speed corresponding to the pressure in the balloon 92. If the balloon pressure is maintained at this pressure level P3' even when the balloon 92 is shifted from the deflated condition to the inflated condition, the pressure differential may be unnecessarily increased. In this case, it may be difficult to inflate the balloon 92 at a quick inflating speed. In light of foregoing, the pressure in the balloon 92 is increased to the pressure P4 when the balloon 92 is estimated to have completely deflated at the pressure P3'. The pressure P4 is substantially equal to or higher than the maximum pressure and is higher than the pressure P3'. Accordingly, the pressure differential upon inflating the balloon 92 can be decreased. Therefore, the balloon inflation can be performed quickly.

As described above, according to the first embodiment of the present invention, the balloon inflating/deflating response can be effectively improved by assuring the quick deflating response and the quick inflating response for the next balloon inflation.

The pressure P3' can be set at any pressure level between the maximum pressure value at which the balloon 92 can be maintained at the deflated condition and the minimum pressure value at which the balloon 92 can be maintained at the deflated condition. However, the lower the pressure P3' is set, the more quickly the balloon 92 can be deflated. Therefore, it is preferable that the pressure P3' be proximate to the minimum pressure value.

As far as the pressure P4 is higher than the pressure P3', the pressure P4 can be set at any pressure level between the maximum pressure value at which the balloon 92 can be maintained at the deflated condition and the minimum pressure value at which the balloon 92 can be maintained at the deflated condition. However, the higher the pressure P4 is set, the pressure differential upon the next balloon inflation can be reduced. Therefore, it is preferable that the pressure P4 be proximate to the maximum pressure value.

The balloon pump driving apparatus 10 according to the first embodiment of the present invention includes inflation judging means (step S102) for judging a timing for inflating the balloon 92 based upon an inputted bio signal, first inflation pressure applying means (step S103, the isolator 40, the pressure control valve 52) for applying a first inflation pressure to the balloon 92 at an appropriate timing judged by the inflation judging means, the first inflation pressure being higher than the minimum pressure value at which the balloon 92 can be maintained at the inflated condition, complete inflation estimating means (step S107) for estimating whether the balloon 92 has completely inflated by having applied the first inflation pressure to the balloon 92 by the first inflation pressure applying means, and second inflation pressure applying means (step S108, the isolator 40, the pressure control valve 52) for applying a second inflation pressure to the balloon 92 when the complete inflation estimating means estimates that the balloon 92 has completely inflated, the second inflation pressure being substantially equal to or higher than the minimum pressure value and lower than the first inflation pressure applied by the first inflation pressure applying means. Therefore, the pressure in the balloon can be decreased.

That is, the pressure P1 is applied to the balloon 92 by the first inflation pressure applying means when the inflation judging means judges that it is a time to inflate the balloon 92. The pressure Pb in the balloon 92 is set at the pressure P1', which is higher than the minimum pressure value and is substantially equal to or lower than the maximum pressure value. As described above, even when the balloon 92 has reached to the completely inflated condition by the first inflation pressure applying means, the balloon 92 can be still applied with the pressure that is higher than the minimum pressure required for maintaining the balloon 92 under the inflated condition. Therefore, the balloon inflation can be performed at a still faster inflating speed.

When the complete inflation estimating means estimates that the balloon 92 has completely inflated, the balloon 92 is applied with the pressure P2 by the second inflation pressure applying means. The applied pressure P2 is substantially equal to or higher than the minimum pressure capable of maintaining the balloon 92 at the inflated condition, and but is lower than the pressure P1 applied by the first inflation pressure applying means. Therefore, the pressure in the balloon 92 is reduced by the second inflation pressure applying means. In this case, the pressure differential upon the next balloon deflation can be reduced. Therefore, the following balloon deflation can be quickly performed. Therefore, the quick inflation response upon the balloon inflation can be ensured, while the quick balloon deflation response upon the following balloon deflation can be ensured. That is, the balloon response can be improved.

The pressure P1 applied by the first inflation pressure applying means is designed to set the pressure in the completely inflated balloon 92 within a range of the pressure P1'. For example, when the first inflation pressure applying means always applies a constant pressure to the balloon 92, the pressure applied to the balloon 92 substantially corresponds to the pressure P1'. On the other hand, the first inflation pressure applying means applies the first inflation pressure to the balloon through a space having a constantly limited volume, according to the first embodiment of the present invention. In this case, the pressure itself is reduced while passing through the space. That is, the applied pressure is reduced with time. The pressure immediately after being applied by the first inflation pressure applying means can be different from the pressure applied to the balloon approaching to the completely inflated condition. In this case, the initially applied pressure is set higher than the pressure P1'. In any case, it is preferable that the balloon 92 be applied with a pressure so as to bring the pressure in the completely inflated balloon 92 to the pressure P1'.

The pressure P2 applied by the second inflation pressure applying means is designed to set the pressure in the deflating balloon 92 within a range of the pressure P2'. For example, when the second inflation pressure applying means always applies a constant pressure to the balloon 92, the pressure applied to the balloon 92 substantially corresponds to the pressure P2'. On the other hand, the second inflation pressure applying means applies the second inflation pressure through the space having the constantly limited volume to the balloon 92, according to the first embodiment of the present invention. In this case, the second inflation pressure itself is increased while passing through the space. That is, the applied pressure is increased with time. The pressure immediately after being applied by the second inflation pressure applying means can be different from the balloon pressure in a predetermined period of time. In this case, the initially applied pressure is lower than the pressure P2'. In any case, it is preferable that the balloon 92 be applied with a pressure so as to bring the pressure in the balloon 92 to the pressure P2'.

The balloon pump driving apparatus 10 according to the first embodiment of the present invention includes deflation judging means (step S113) for judging a timing for deflating the balloon 92 based upon the inputted bio signal, first deflation pressure applying means (step S114, the isolator 40, the pressure control valve 52) for applying a first deflation pressure to the balloon 92 at an appropriate timing judged by the deflation judging means, the first deflation pressure being lower than the maximum pressure at which the balloon 92 can be maintained at the deflated condition, complete deflation estimating means (step S115) for estimating whether the balloon 92 has completely deflated by applying the pressure to the balloon 92 by the first deflation pressure applying means, and second deflation pressure applying means (step S116, the isolator 40, the pressure control valve 52) for applying a second deflation pressure to the balloon 92 when the complete deflation estimating means estimates that the balloon 92 has completely deflated, the second deflation pressure being substantially equal to or lower than the maximum pressure value and higher than the pressure applied by the first deflation pressure applying means.

That is, the pressure P3 is applied to the balloon 92 by the first deflation pressure applying means when the deflation judging means judges that it is a time to deflate the balloon 92. The pressure in the balloon 92 is set at the pressure P3' which is lower than the maximum pressure value and is substantially equal to or higher than the minimum pressure value. As described above, even when the balloon 92 has reached to the completely deflated condition by the first deflation pressure applying means, the balloon 92 can be still applied with the pressure that is lower than the maximum pressure required for deflating the balloon 92. Therefore, the balloon deflation can be performed at a still faster deflating speed.

When the complete deflation estimating means estimates that the balloon 92 has completely deflated, the balloon 92 is applied with the pressure P4 by the second deflation pressure applying means. The applied pressure P4 is substantially equal to or lower than the maximum pressure capable of maintaining the balloon 92 at the deflated condition, and but is higher than the pressure P3 applied by the first deflation pressure applying means. Therefore, the pressure in the balloon 92 is increased by the second deflation pressure applying means. In this case, the pressure differential upon the next balloon inflation can be reduced. Therefore, the following balloon inflation can be quickly performed. Therefore, the quick deflation response upon the balloon deflation can be ensured, while the quick balloon inflation response upon the following balloon inflation can be ensured. That is, the balloon response can be effectively improved.

The pressure P3 applied by the first deflation pressure applying means is designed to set the pressure in the completely deflated balloon 92 within a range of the pressure P3'. For example, when the first deflation pressure applying means always applies a constant pressure to the balloon 92, the pressure applied to the balloon 92 substantially corresponds to the pressure P3'. On the other hand, the first deflation pressure applying means applies a first deflation pressure through a space having a constantly limited volume to the balloon 92, according to the first embodiment of the present invention. In this case, the first deflation pressure itself is increased while passing through the space. That is, the applied pressure is increased with time. The pressure immediately after being applied by the first deflation pressure applying means can be different from the pressure applied to the balloon approaching to the completely deflated condition. In this case, the initially applied pressure is lower than the pressure P3'. In any case, it is preferable that the balloon 92 be applied with a pressure so as to bring the pressure in the completely deflated balloon 92 to the pressure P3'.

The pressure applied by the second deflation pressure applying means is designed to set the pressure in the balloon 92 within a range of the pressure P4. For example, when the second deflation pressure applying means always applies a constant pressure to the balloon 92, the pressure applied to the balloon 92 substantially corresponds to the pressure P4. On the other hand, the second deflation pressure applying means applies a second deflation pressure through the space having the constantly limited volume to the balloon 92, according to the first embodiment of the present invention. In this case, the second deflation pressure itself is decreased while passing through the space. That is, the applied pressure is decreased with time. The pressure immediately after being applied by the second deflation pressure applying means can be different from the balloon pressure in a predetermined period of time. In this case, the initially applied pressure is higher than the pressure P4. In any case, it is preferable that the balloon 92 be applied with a pressure so as to bring the pressure in the balloon 92 to the pressure P4.

According to the first embodiment of the present invention, in response to the opening operation of the pressure control valve 52 after accumulating the first inflation pressure P1 in the isolator 40, the first inflation pressure P1 is applied to the balloon 92 such that the balloon 92 is inflated. In the elapsed time T1 set after the opening operation of the pressure control valve 52, the pressure control valve 52 is closed, and the pressure Pi in the isolator 40 is decreased. When the controller 70 estimates that the balloon 92 has completely inflated, the pressure control valve 52 is opened again. In this case, the isolator 40 communicates with the balloon 92. However, since the pressure Pi in the isolator 40 has been decreased, the pressure in the balloon 92 is also decreased. In the elapsed time T2 after the opening operation of the pressure control valve 52, the pressure control valve 52 is closed. As described above, according to the first embodiment of the present invention, the balloon 92 can be applied with a pressure higher than the minimum pressure required for inflating the balloon 92 even when the balloon 92 has been completely inflated. Therefore, the balloon 92 can be inflated at a further faster inflating speed.

When the controller 70 estimates that the balloon 92 has completely inflated, the pressure control valve 52 is opened again. In this case, the isolator 40 communicates with the balloon 92. However, since the pressure Pi in the isolator 40 has been decreased, the pressure in the balloon 92 is also decreased. Therefore, the pressure differential upon the following deflation can be decreased, thereby not hindering the following quick deflation. As described above, according to the first embodiment of the present invention, the quick inflation response upon the balloon inflation can be ensured, while the quick balloon deflation response upon the following balloon deflation can be ensured. Overall, the balloon inflating/deflating response can be effectively improved.

If sufficient pressure for completely inflating the balloon 92 at a predetermined pressure level is supplied to the balloon 92 from the pressure accumulator while the communication between the isolator 40 and the balloon 92 has been established with the opened pressure control valve 52, there is no need to keep the communication between the isolator 40 and the balloon 92. Rather than keeping the communication therebetween, it is preferable that the pressure control valve 52 is closed after opening the pressure control valve 52 for the predetermined elapsed time, and the pressure in the isolator 40 is decreased while the pressure control valve 52 is closed. In this case, the balloon can be quickly applied with the decreased balloon when the pressure control valve 52 is next opened. In light of foregoing, according to the first embodiment of the present invention, the balloon 92 is first applied with the first inflation pressure P1 by opening the pressure control valve 52. When the controller 70 estimates that the balloon 92 has completely inflated after closing the pressure control valve 52, the pressure lower than the first inflation pressure P1 is applied to the balloon 92 by opening the pressure control valve 52 again. Therefore, the pressure decrease in the balloon 92 can be smoothly performed. Further, the period for which the balloon 92 is applied with a relatively high pressure can be reduced, thereby enabling to improving durability of the balloon 92.

Further, according to the first embodiment of the present invention, the time TV is corrected based upon the pressure being applied to the balloon 92 after closing the pressure control valve 52. Therefore, the inflation pressure in the balloon 92 can be accurately maintained.

According to the first embodiment of the present invention, in response to the opening operation of the pressure control valve 52 after accumulating the first deflation pressure in the isolator 40, the first deflation pressure is applied to the balloon 92 such that the balloon 92 is deflated. When the controller 70 estimates that the balloon 92 has completely deflated, the pressure accumulated in the isolator 40 is increased. The pressure control valve 52 is then closed when the pressure in the balloon 92 reaches the predetermined pressure. As described above, according to the first embodiment of the present invention, the balloon 92 can be applied with a pressure lower than the maximum pressure required for deflating the balloon 92 even when the balloon 92 has been completely deflated. Therefore, the balloon 92 can be deflated at a further faster deflating speed.

When the controller 70 estimates that the balloon 92 has completely deflated, the pressure in the balloon 92 is increased. In this case, the pressure differential upon the following inflation can be decreased, thereby not hindering the following quick inflation. As described above, according to the first embodiment of the present invention, the quick deflation response upon the balloon deflation can be ensured, while the quick balloon inflation response upon the following balloon inflation can be ensured. Overall, the balloon inflating/deflating response can be effectively improved.

Next, following explanation will be given for explaining the balloon pump driving apparatus according to a second embodiment of the present invention with reference to FIGS. 4, 5, 6 and 6B. The fundamental structure of the balloon pump driving apparatus 10 according to the second embodiment is substantially identical to the one according to the first embodiment. A major difference therebetween is that the balloon pump driving apparatus according to the second embodiment is additionally provided with an auxiliary reservoir tank communicating with the output conduit 51. Accordingly, explanation of the identical portions to the first embodiment of the present invention will be omitted herein, and the identical portions are denoted with the identical reference numerals.

Figure 4:
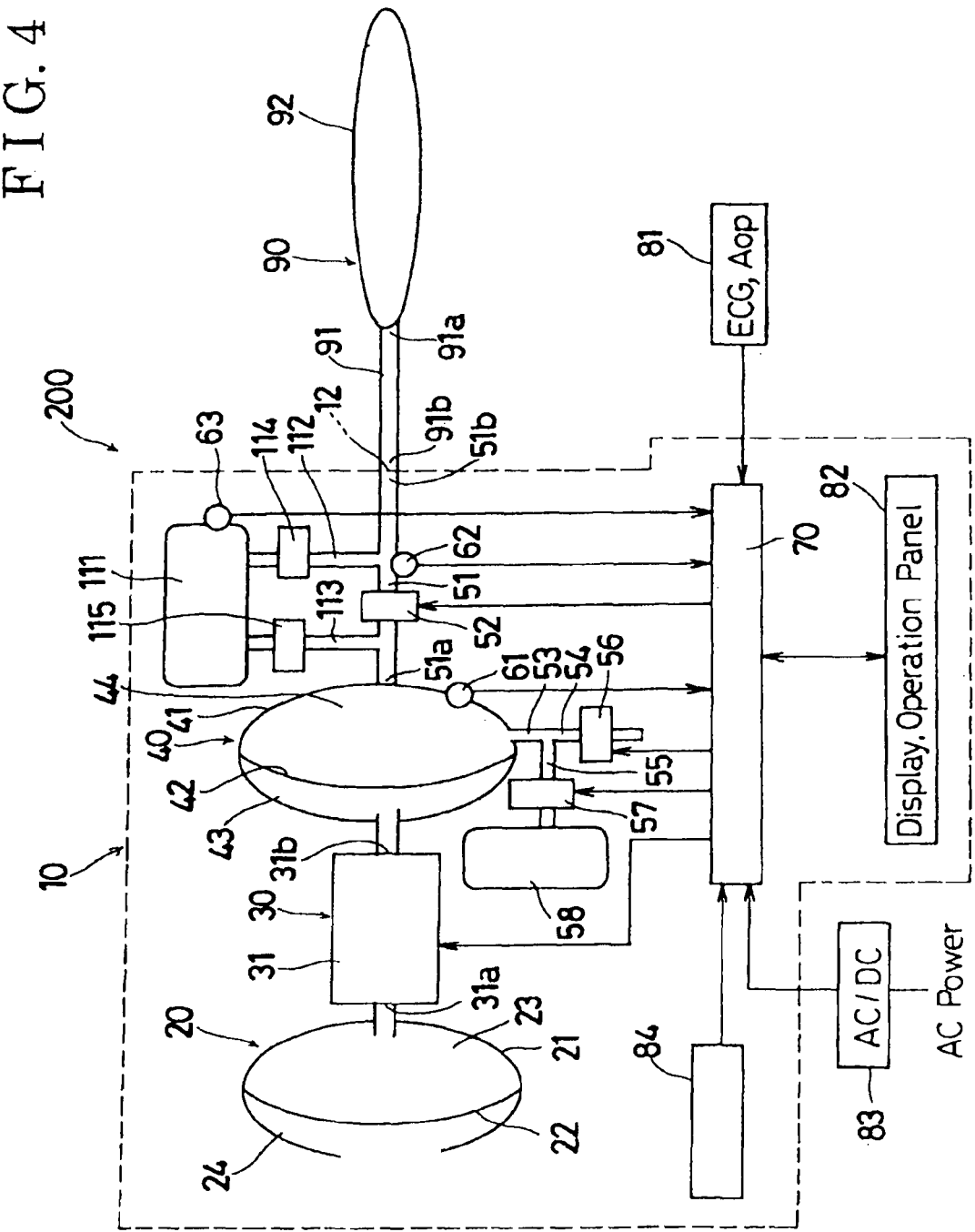
FIG. 4 is a schematic view illustrating a balloon pumping system according to a second embodiment of the present invention.

With reference to FIG. 4, a balloon pumping system 200 according to the second embodiment of the present invention includes the balloon catheter 90 and the balloon pump driving apparatus 10. The structure of the balloon catheter 90 is substantially identical to the one according to the first embodiment of the present invention, so that the explanation thereof will be omitted herein for simplifying the explanation.

The balloon pump driving apparatus 10 is provided with the outer shell of the apparatus housing 11 which houses the oil reservoir 20, the oil pump 30, and the isolator 40. The respective structures of the oil reservoir 20, the oil pump 30 and the isolator 40 are identical to the ones according to the first embodiment of the present invention, so that the explanation thereof will be omitted herein for simplifying the explanation.

In the same manner as the first embodiment of the present invention, the output chamber 44 communicates with the one end 51a of the output conduit 55, while the other end 51b of the output conduit 51 communicates with the output port 12 formed at the surface of the apparatus housing 11. The output port 12 is connected to the proximal end 91b of the catheter 91, such that the balloon catheter 90 communicates with the output conduit 51.

The pressure control valve 52 is disposed in the output conduit 51. The structure of the pressure control valve 52 is the same as the one according to the first embodiment.

The first pressure sensor 61 is equipped in the output chamber 44 of the isolator 40 so as to detect the pressure in the output chamber 44. The second pressure sensor 62 is equipped at the downstream side of the pressure control valve 52 at the output conduit 51, i.e., at the side near the balloon catheter 90.

One ends of first auxiliary conduit (i.e., a first connecting passage) 112 and second auxiliary conduit 113 are connected to the output conduit 51, respectively. More particularly, the communication between the first auxiliary conduit 112 and the output conduit 51 is established at a portion between the pressure control valve 52 and the output port 12. The communication between the second auxiliary conduit 113 and the output conduit 51 is established at a portion between the output chamber 44 and the pressure control valve 52. The other ends of the first and second auxiliary conduits 112 and 113 are connected to an auxiliary reservoir tank 111, respectively. A first auxiliary switching valve 114 is disposed in the first auxiliary conduit 112, while a second auxiliary switching valve 115 is disposed in the second auxiliary conduit 113. The auxiliary reservoir tank 111 has been charged with helium gas. The internal pressure in the auxiliary reservoir tank 111 is detected by a third pressure sensor 63.

As illustrated in FIG. 4, the balloon pump driving apparatus 10 includes the controller 70. The controller 70 is electrically connected to the driving means of the oil pump 30, the supply switching valve 57, the drain switching valve 56, the pressure control valve 52, the first auxiliary switching valve 114, the second auxiliary switching valve 115, the first pressure sensor 61, the second pressure sensor 62, and the third pressure sensor 63. The controller 70 is further electrically connected to the biological signal output device 81 and the display-operating panel 82. The biological signal output device 81 outputs the ECG signal and/or the Aop signal to the controller 70. The controller 70 is still further connected to the AC/DC adapter 83 connected to the normal alternator and the battery 84 as the auxiliary power source.

The oil chamber 23 of the oil reservoir 20 has been charged with oil, in the same manner as the first embodiment. That is, the primary space defined by the oil chamber 23 of the oil reservoir 20, the pumping chamber of the oil pump 30, and the input chamber 43 of the isolator 43 can be charged with the oil. The output chamber 44 has been charged with helium gas, in the same manner as the first embodiment.

Next, the operation of the balloon pumping system 200 will be explained hereinbelow with reference to FIGS. 5, 6A, and 6B. As explained by a timing chart illustrated in FIG. 5, a sequential line graph denoted with a solid line explains how the pressure Pi in the output chamber 44 detected by the first pressure sensor 61 transits, while a sequential line graph denoted with a dotted line explains how the pressure Pb detected by the second pressure sensor 62 transits. The pressure Pb substantially corresponds to the pressure in the balloon 92. A sequential line graph denoted with a chain line explains how a pressure Pr in the auxiliary reservoir lank 111 transits. The balloon pumping system 200 repeats inflation and deflation of the balloon 92, such that there is no clear definition of a starting point. Therefore, the following explanation will be initialed from a point Q in FIG. 5, i.e., from a condition where the pressure control valve 52, the first auxiliary switching valve 114, and the second auxiliary switching valve 115 are closed, the balloon 92 has deflated with the applied pressure Pb at the second deflation pressure P4, and the pressure in the auxiliary reservoir tank 111 is set at an auxiliary pressure P5.

Figure 5:
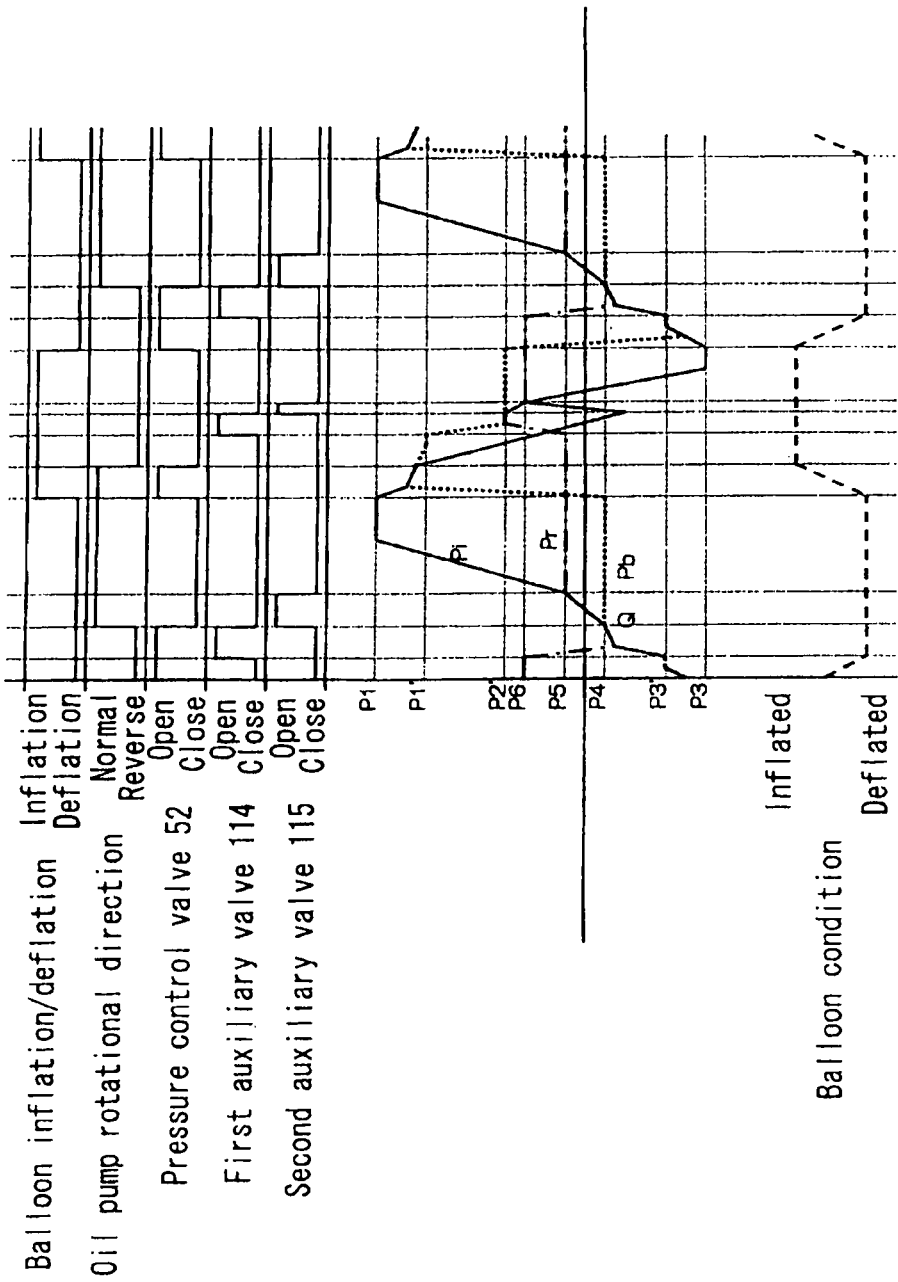
FIG. 5 is a timing chart for explaining transitions of the timing for inflating and deflating the balloon, the inflated and deflated condition of the balloon, the rotational direction of the oil pump, the timing for switching the pressure control valve, the timings for switching first and second switching valves, the pressure in the output chamber, the pressure applied to the balloon, and a pressure in an auxiliary reservoir tank according to the second embodiment of the present invention.
Figure 6A:
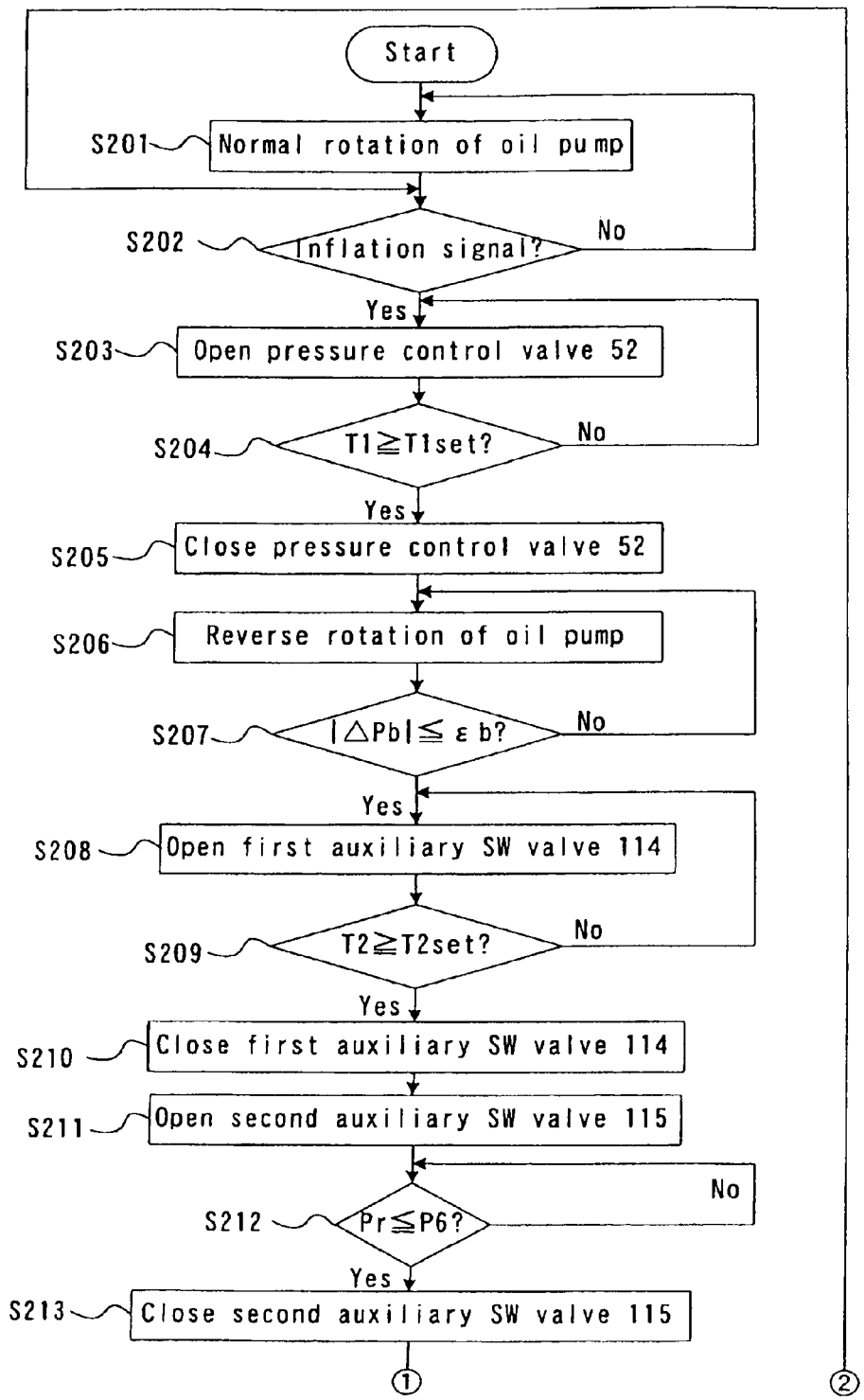
FIGS. 6A and 6B are a main flowchart of the controller for inflating and deflating the balloon by the balloon pumping system illustrated in FIG. 4.
Figure 6B:
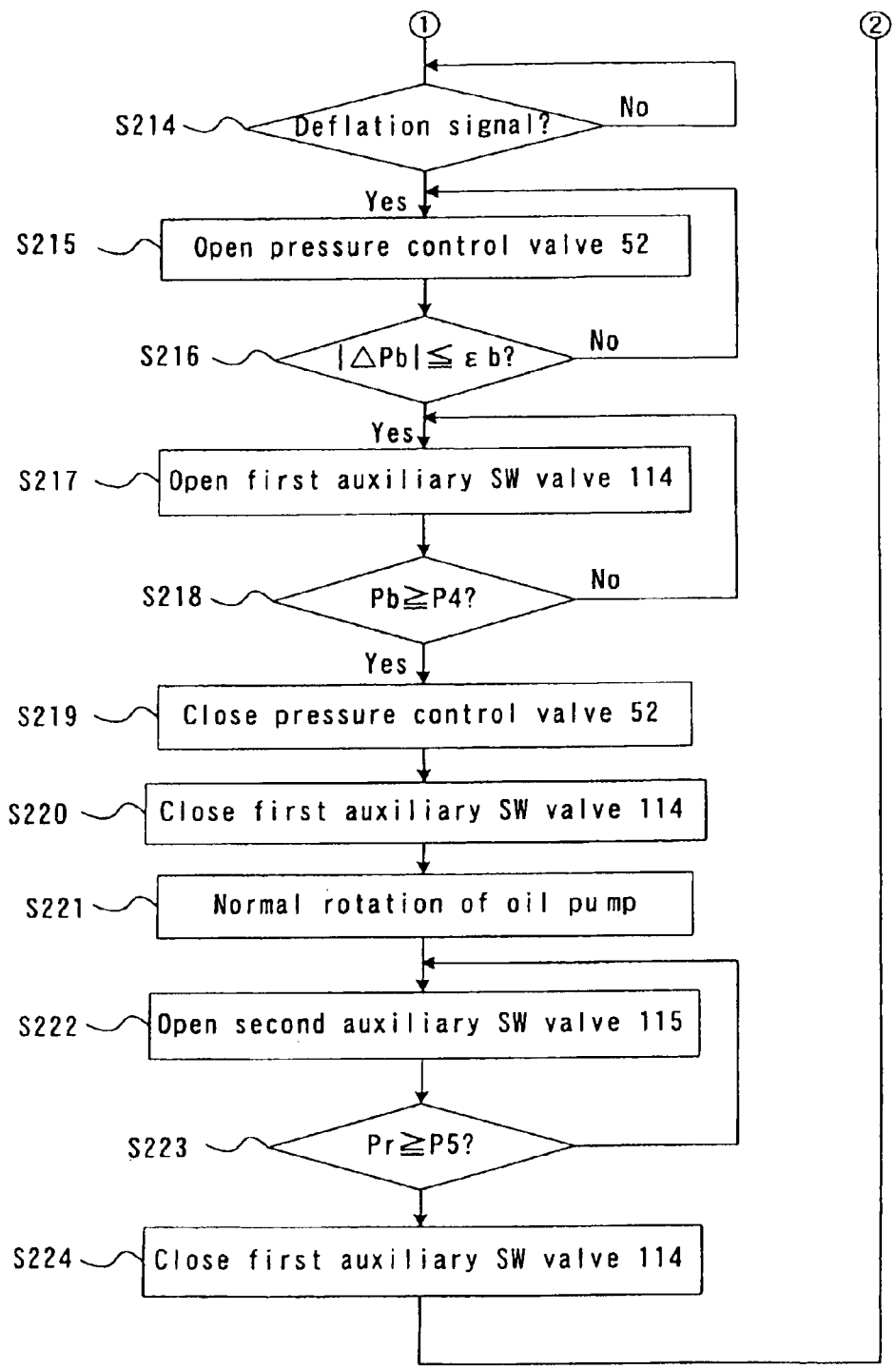

Under the above-described condition, the oil pump 30 is driven for rotation in the normal direction as explained at step S201 in FIG. 5. In response to the normal rotation of the oil pump 30, the oil in the oil reservoir 20 is introduced to the oil pump 30 through the first I/O port 31a. The oil is then drained to the input chamber 43 of the isolator 40 through the second I/O port 31b. In this case, the isolator diaphragm 42 moves and extends in a right direction in FIG. 4. In response to the extension of the isolator diaphragm 42, the volume of the output chamber 44 is decreased such that the pressure Pi of the output chamber 44 is detected at an increased pressure value by the first pressure sensor 61. When the pressure Pi in the output chamber 44 reaches the first inflation pressure P1, the rotational speed of the oil pump 30 is slowed down so as not to increase the pressure Pi any more. The amount of oil discharged from the oil pump 30 to the isolator 40 can be balanced with the amount of oil flowing back from the isolator 40 to the oil pump 30. Accordingly, the pressure Pi in the output chamber 44 can be maintained at the first inflation pressure P1 (the first inflation pressure control). The first inflation pressure P1 is far higher than the pressure required for inflating the balloon 92.

At step S202, the controller 70 judges the presence or absence of the inflation signal for the balloon 92 (inflation judging means). When the controller 70 judges that the inflation signal has not been outputted, the program returns to step S201. When the controller 70 judges that the inflation signal has been outputted, the program proceeds to step S203.

When the inflation signal is outputted at step S202, the controller 70 recognizes that the balloon 92 is under the inflating period, i.e., the balloon 92 is shifting from the deflated condition to the inflated condition. At step S203, the controller 70 outputs the command signal for opening the pressure control valve 52 (the inflation-time valve opening control). In response to the opening operation of the pressure control valve 52, the output chamber 44 of the isolator 40 communicates with the balloon 92 such that the first inflation pressure P1 in the output chamber 44 is applied to the balloon 92. In this case, the pressure Pb is rapidly increased from the second deflation pressure P4.

As described above, the output chamber 44 has been charged with the first inflation pressure P1 higher than the pressure required for inflating the balloon 92 until the timing immediately before the pressure control valve 52 is opened. Therefore, once the pressure control valve 52 is opened, the helium gas in the output chamber 44 at a blast flows into the balloon 92. Therefore, according to the second embodiment of the present invention, the balloon 92 can be inflated much faster than conventional methods.

The program then proceeds to step S204 after opening the pressure control valve 52, at which the controller 70 judges whether the pressure control valve 52 has opened for the set period T1set, i.e., judges whether the opening period T1 of the pressure control valve 52 is substantially equal to or greater than the set period T1set (the T1 judging control). When the controller 70 judges that the opening period T1 has not reached the set period T1set, the program returns to step S203. In the meantime, when the controller 70 judges that the opening period T1 has reached the set period T1set, the program proceeds to step S205.

At step S205, the controller 70 closes the pressure control valve 52 (the inflation-time intermediate valve closing control). The communication between the output chamber 44 and the balloon 92 is interrupted in response to the closing operation of the pressure control valve 52. The program then proceeds to step S206.

At step S206, the controller 70 drives the oil pump 30 for rotation in the reverse direction. The oil in the input chamber 43 in the isolator 40 is then sucked into the oil pump 30 through the second I/O port 31b. The oil in the oil pump 30 is then drained into the oil chamber 23 of the oil reservoir 20 through the first I/O port 31a. Therefore, the isolator diaphragm 42 then moves in a left direction in FIG. 4. The volume of the output chamber 44 is increased corresponding to the movement of the diaphragm 42 such that the pressure Pi in the output chamber 44 is decreased as explained in FIG. 5 (the pressure decrease control).

The pressure change rate (with time) of the pressure value Pb detected by the second pressure sensor 62 is denoted with the pressure change rate $\ddot{A}Pb$ with time. At step S207, the controller 70 judges whether the pressure change rate $\ddot{A}Pb$ is zero or within a predetermined range åb.

When the pressure change rate $\ddot{A}Pb$ is judged to have not been substantially equal to zero or to have not been within the range åb at step S207, the controller 70 judges that the balloon 92 has not been completely inflated yet. Therefore, the program returns to step S206. When the pressure change rate $\ddot{A}Pb$ is judged to have been substantially equal to zero or to have been within the range åb at step S207, the program proceeds to step S208.

As explained in FIG. 5, according to the second embodiment of the present invention, the pressure change rate $\overline{A}Pb$ becomes approximately zero during the inflating period. In this case, the pressure Pb has reached the pressure P1'. The pressure P1' is higher than the minimum pressure value capable of maintaining the balloon 92 at the inflated condition, and is lower than the maximum pressure value capable of maintaining the balloon 92 at the inflated condition. On the other hand, according to a conventional balloon pump driving apparatus, the pressure in the balloon is set around the minimum pressure level capable of maintaining the balloon under the inflated condition when the balloon is completely inflated. Comparing the balloon pump driving apparatus 10 with this type of conventional balloon pump driving apparatus, the balloon 92 can be inflated faster because the balloon 92 has been applied with the pressure P1' higher than the conventional applied pressure even when the balloon 92 has completely inflated. It is preferable that the pressure P1' be set at a pressure value proximate to the maximum pressure value capable of maintaining the balloon 92 at the inflated condition. That is, it is preferable that the pressure P1' be set at a pressure value as high as possible within the allowable pressure range. By setting the pressure P1' at a relatively high value as described above, the balloon 92 can be effectively inflated at a much faster inflating speed.

When the pressure change rate ΔPb is judged to have been substantially equal to zero or to have been within the range åb at step S207, the program proceeds to step S208, wherein the auxiliary switching valve 114 is opened (the inflation-time intermediate valve opening control). In response to the opening operation of the auxiliary switching valve 114, the communication between the auxiliary reservoir tank 111 and the balloon 92 is established. The pressure Pr in the auxiliary reservoir tank 111 has been set at an inflation auxiliary pressure P5 until a timing immediately before the first auxiliary switching valve 114 is opened. As explained in FIG. 5, the pressure P5 is lower than the pressure P1'. Therefore, when the first auxiliary switching valve 114 is opened, the helium gas in the balloon 92 flows into the auxiliary reservoir tank 111, wherein the pressure Pb applied to the balloon 92 is quickly decreased.

The program then proceeds to step S209 after opening the first auxiliary switching valve 114 at step S208. At step S209, the controller 70 judges whether the first auxiliary switching valve 114 has opened for the set period T2set, i.e., judges whether the opening period 12 of the first auxiliary switching valve 114 is substantially equal to or greater than the set period T2set. When the controller 70 judges that the opening period T2 has not reached the set period T2set, the program returns to step S208. When the controller 70 judges that the opening period T2 has reached the set period T2set, the program proceeds to step S210.

At step S210, the controller 70 closes the first auxiliary switching valve 114 (the inflation-time valve closing control). The communication between the auxiliary reservoir tank 111 and the balloon 92 is interrupted in response to the closing operation of the first auxiliary switching valve 114. The balloon 92 is then maintained under the inflated condition at the applied pressure P2'. The program then proceeds to step S211. Through steps S207, S208, and S209, the pressure Pb applied to the balloon 92 is set at the pressure P2'. This pressure can be estimated as the pressure in the balloon 92. Therefore, the balloon 92 is maintained under the inflated condition at the pressure P2'. It is preferable that the pressure P2' be set at a value proximate to the minimum pressure value capable of maintaining the balloon 92 under the inflated condition. That is, it is preferable that the pressure P2' be set at a pressure value as low as possible within the allowable pressure range. By setting the pressure P2' at a low value as described above, a pressure differential can be minimized when the balloon 92 is shifted from the inflated condition to the deflated condition.

At step S211, the controller 70 opens the second auxiliary switching valve 115. The communication between the auxiliary reservoir tank 111 and the output chamber 44 is established. At this point, the oil pump 30 has rotated in the reverse direction. Therefore, the pressure Pi in the output chamber 44 has decreased. Further, the pressure Pi in the output chamber 44 is lower than the pressure Pr in the auxiliary reservoir tank 111 (in this case, the pressure Pr is the pressure P2'). Therefore, the helium gas in the auxiliary reservoir tank 111 is sucked into the output chamber 44 in response to the opening operation of the second auxiliary switching valve 115, wherein the pressure Pr in the auxiliary reservoir tank 111 is decreased.

The program then proceeds to step S212 after opening the second auxiliary switching valve 115. At step S212, the controller 70 judges whether the pressure Pr in the auxiliary reservoir tank 111 has decreased to a predetermined pressure P6. When the controller 70 judges that the pressure Pr in the auxiliary reservoir tank 111 has not decreased to the predetermined pressure P6, the program returns to step S212. On the other hand, when the controller 70 judges that the pressure Pr in the auxiliary reservoir tank 111 has decreased to the predetermined pressure P6, the program proceeds to step S213, at which the second auxiliary switching valve 115 is closed. In response to the closing operation of the second auxiliary switching valve 115, the communication between the auxiliary reservoir tank 111 and the output chamber 44 is interrupted. As described above, the pressure Pr in the auxiliary reservoir tank 111 is set approximately at the predetermined pressure P6 (an auxiliary reservoir pressure setting control). It is preferable to set the pressure Pr approximately at the predetermined pressure P6 when the pressure Pb in the balloon 92 is set at the second deflation pressure P4 (described later).

The oil pump 30 has still rotated in the reverse direction even after closing the second auxiliary switching valve 115 at step S210. In this case, the isolator diaphragm 42 has expanded in the left direction in FIG. 4, wherein the volume of the output chamber 44 is increased. In this case, the pressure Pi in the output chamber 44 is further decreased down to the first deflation pressure P3. The rotational speed of the oil pump 30 in the reverse direction is slowed down to prevent occurrence of a further pressure decrease in the output chamber 44. The amount of oil introduced from the isolator 40 to the oil pump 30 is substantially balanced with the amount of oil flown back to the isolator 40 from the oil pump 30. Therefore, the pressure Pi in the output chamber 44 can be maintained at the first deflation pressure P3 (the first deflation pressure control). The first deflation pressure P3 is designed to be far lower than the pressure required for deflating the balloon 92.

At step S214, the controller 70 judges the presence or absence of the deflation signal of the balloon 92 (the deflation judging means). In the same manner as the judgment of the presence of absence of the inflation signal, the controller 70 computes the timing for deflating the balloon 92, which is appropriate for the body condition of the patient, based upon the ECG signal and/or the Aop signal. The controller 70 outputs the deflation signal in response to the computed timing. When the controller 70 judges that the deflation signal has not been outputted, the program returns to step S212. When the controller 70 judges that the deflation signal has been outputted, the program proceeds to step S215.

When the deflation signal is outputted at step S214, the controller 70 recognizes that the balloon 92 is under the deflating period, i.e., the balloon 92 is shifted from the inflated condition to the deflated condition. At step S215, the controller 70 outputs a command signal for opening the pressure control valve 52 (the deflation-time valve opening control). In response to the opening operation of the pressure control valve 52, the output chamber 44 of the isolator 40 communicates with the balloon 92. The first deflation pressure P3 accumulated in the output chamber 44 is then applied to the balloon 92 so that the pressure Pb in the balloon 92 is suddenly decreased from the second inflation pressure P2'. The output chamber 44 has been charged with the first inflation pressure P3 until timing immediately before the opening operation of the pressure control valve 52. Therefore, in response to the opening operation of the pressure control valve 52, the helium gas at a blast flows from the balloon 92 to the output chamber 44. Therefore, according to the second embodiment of the present invention, the deflation of the balloon 92 can be performed faster than the conventional balloon pumping system.

After opening the pressure control valve 52 at step S215, the program proceeds to step S216, at which the controller 70 judges whether the pressure change rate ÄPb of the pressure Pb for the balloon 92 is substantially zero or within the predetermined range åb (the complete deflation estimating means). That is, the controller 70 judges whether the balloon 92 has completely deflated in the same manner as the first embodiment of the present invention. When the controller 70 judges at step S216 that the pressure change rate $\overline{A}$Pb for the balloon 92 is not substantially zero or not within the predetermined range åb, the program returns to step S216. On the other hand, when the controller 70 judges at step S216 that the pressure change rage $\overline{\Delta Pb}$ for the balloon 92 is substantially zero or within the predetermined rage åb, the program proceeds to step S217.

As explained in FIG. 5, according to the second embodiment of the present invention, the pressure change rate $\overline{\Delta Pb}$ becomes approximately zero during the deflating period. In this case, the pressure Pb has reached the pressure P3'. The pressure P3' is lower than the maximum pressure value capable of maintaining the balloon 92 at the deflated condition, and is higher than the minimum pressure value capable of maintaining the balloon 92 at the deflated condition. On the other hand, according to a conventional balloon pump driving apparatus, the pressure in the balloon is set around the maximum pressure level capable of maintaining the balloon under the deflated condition when the balloon is completely deflated. Comparing the balloon pump driving apparatus 10 with a conventional balloon pump driving apparatus, the balloon 92 can be deflated faster because the balloon 92 has been applied with the pressure P3' lower than the conventional applied pressure even when the balloon 92 has completely deflated. Therefore, the balloon deflation can be performed quickly. It is preferable that the pressure P3' be set at a pressure value proximate to the minimum pressure value capable of maintaining the balloon 92 at the deflated condition. By setting the pressure P3' at a relatively low value as described above, the balloon 92 can be effectively deflated at a much faster deflating speed.

When the pressure change rate $\overline{\Delta Pb}$ is judged to have been substantially equal to zero or to be within the range åb, the program proceeds to step S217, wherein the first auxiliary switching valve 114 is opened (the deflation-time intermediate valve opening control). The communication between the auxiliary reservoir tank 111 and the balloon 92 is established in response to the opening operation of the first auxiliary switching valve 114. The pressure Pr in the auxiliary reservoir tank 111 has been set at the deflation auxiliary pressure P6 until the timing immediately before the opening operation of the first auxiliary switching valve 114. As explained in FIG. 5, the pressure P6 is higher than the pressure P3' of the pressure Pb of the balloon 92. Therefore, when the first auxiliary switching valve 114 is opened, the helium gas in the auxiliary reservoir tank 111 flows into the balloon 92, thereby rapidly increasing the pressure Pb.

The program then proceeds to step S218 after opening the first auxiliary switching valve 114 at step S217. At step S218, the controller 70 judges whether the pressure Pb of the balloon 92 has reached the pressure P4. When the pressure Pb has not reached the pressure P4, the program returns to step S217. On the other hand, when the pressure Pb has reached the pressure P4, the program proceeds to step S219, wherein the pressure control valve 52 is closed (the deflation-time valve closing control). In response to the closing operation of the pressure control valve 52, the communication between the output chamber 44 and the balloon 92 is interrupted. Therefore, the pressure Pb of the balloon 92 is maintained at the pressure P4. As described above, through steps S217, S218, and S219, the pressure Pb is set at the pressure P4 while the balloon 92 is deflating. This pressure can be estimated as a pressure in the balloon 92 at this moment. Therefore, the balloon 92 can be maintained under the deflated condition at the pressure P4. It is preferable that the pressure P4 be set proximate to the maximum pressure capable of maintaining the balloon 92 under the deflated condition. By setting the pressure P4 at a relatively high pressure as described above, the pressure differential can be minimized when the balloon 92 is shifted from the deflated condition to the inflated condition.

The first auxiliary switching valve 114 is closed at step S220 substantially at the same time when the pressure control valve 52 is closed at step S219 or after the closing operation at step S219. The communication between the balloon 92 and the auxiliary reservoir tank 111 is hence interrupted. The program then proceeds to step S221.

At step S221, the oil pump 30 is driven for rotation in the normal direction. The oil in the oil reservoir 20 is suck into the oil pump 30. The oil in the oil pump 30 is drained to the input chamber 43 of the isolator 30. In this case, the isolator diaphragm 42 expands in the right direction in FIG. 4. In response to the movement of the isolator diaphragm 42, the volume of the output chamber 44 is decreased, wherein the pressure Pi in the output chamber 44 is increased (the pressure increase control).

The program then proceeds to step S222 from step S221. At step S222, the second auxiliary switching valve 115 is opened. In response to the opening operation of the second auxiliary switching vale 115, the communication between the auxiliary reservoir tank 111 and the output chamber 44 of the isolator 40 can be established. Since the oil pump 30 is driven for rotation in the normal direction at step S221, the volume of the output chamber 44 is decreased, wherein the pressure Pi in the output chamber 44 is increased. Therefore, when the communication between the output chamber 44 and the auxiliary reservoir tank 111 is established, the pressure Pr in the auxiliary reservoir tank 111 is increased in response to the increase of the pressure Pi in the output chamber 44.

The program then proceeds to step S223 from step S222. At step S223, the controller 70 judges whether the pressure in the auxiliary reservoir tank 11 has reached the predetermined pressure P5. When the pressure Pr has not reached the predetermined pressure P5 yet, the program then returns to step S222. On the other hand, when the pressure Pr has reached the predetermined pressure P5, the program proceeds to step S224. At step S224, the second auxiliary switching valve 115 is closed (inflation-time auxiliary reservoir pressure setting terminate control). In response to the closing operation of the second auxiliary switching valve 115, the communication between the auxiliary reservoir tank 111 and the output chamber 44 is interrupted.

Through steps S222, S223, and S224, the pressure Pr in the auxiliary reservoir tank 111 reaches the predetermined pressure P5 (auxiliary reservoir pressure setting control). It is necessary to maintain the pressure Pr in the auxiliary reservoir tank 111 at the pressure P5 in order to bring the pressure Pb in the balloon 92 to the second inflation pressure P2. The program then returns to step S202. By repeatedly performing the above-described steps, the balloon 92 can be inflated and deflated at a predetermined timing.

As described above, the balloon pumping method of inflating and deflating the balloon 92 according to the second embodiment of the present invention includes the step of setting the pressure Pb in the balloon 92 at the pressure P1', which is higher than the minimum pressure value and substantially equal to or lower than the maximum pressure value, when the balloon 92 is shifted from the deflated condition to the inflated condition. The balloon 92 can be maintained under the inflated condition when the pressure in the balloon 92 is between the minimum pressure value and the maximum pressure value. The balloon pumping method further includes the step of setting the pressure Pb in the balloon 92 at the pressure P2', which is substantially equal to or higher than the minimum pressure value and lower than the pressure P1', when the balloon 92 is estimated to have completely inflated at the pressure P1'. By performing the above-described steps, the balloon 92 can be completely inflated at the pressure P1' which is higher than the minimum pressure at which the balloon 92 is maintained at the inflated condition. Therefore, the inflation of the balloon 92 can be quickly performed. The pressure Pb in the balloon 92 is reduced to the pressure P2' when the balloon 92 is estimated to have completely inflated at the pressure P1'. The pressure P2' is substantially equal to or higher than the minimum pressure and is lower than the pressure P1'. Accordingly, the pressure differential upon deflating the balloon 92 can be decreased, wherein the balloon deflation can be performed quickly. Therefore, according to the second embodiment of the present invention, much faster inflation response can be assured upon the balloon inflation, while quick deflation response can be assured for the next balloon deflation. Overall, the balloon response can be effectively improved.

The balloon pumping method of inflating and deflating the balloon 92 includes the step of setting the pressure in the balloon 92 at the pressure P3', which is lower than the maximum pressure value and is substantially equal to or higher than the minimum pressure value, when the balloon 92 is shifted from the inflated condition to the deflated condition. The balloon pumping method further includes the step of setting the pressure in the balloon 92 at the pressure P4, which is substantially equal to or lower than the maximum pressure value and higher than the pressure P3', when the balloon 92 is estimated to have completely deflated at the pressure value P3'. By performing the above-described steps, the balloon 92 can be completely deflated at the pressure P3' which is lower than the maximum pressure value at which the balloon 92 is maintained under the deflated condition. Therefore, the deflation of the balloon 92 can be quickly performed. By performing the above-described steps, the balloon 92 can be completely deflated at the pressure P3' which is lower than the maximum pressure. Therefore, the deflation of the balloon 92 can be quickly performed. The pressure Pb in the balloon 92 is increased to the pressure P4 when the balloon 92 is estimated to have completely deflated at the pressure P3'. The pressure P4 is substantially equal to or lower than the maximum pressure and is higher than the pressure P3'. Accordingly, the pressure differential upon inflating the balloon 92 can be decreased, wherein the balloon deflation can be performed quickly. Therefore, according to the second embodiment of the present invention, much faster deflation response can be assured upon the balloon deflation, while quick inflation response can be assured for the next balloon inflation. Overall, the balloon response can be effectively improved.

The balloon pump driving apparatus 10 according to the second embodiment of the present invention includes the inflation judging means (step S202) for judging whether the balloon 92 is required to be inflated based upon the inputted bio signal, the first inflation pressure applying means (step S203, the isolator 40, the pressure control valve 52) for applying the first inflation pressure to the balloon 92, which is higher than the minimum pressure at which the balloon 92 can be maintained at the inflated condition, when the inflation judging means judges that it is necessary to inflate the balloon 92, the complete inflation estimating means (step S207) for estimating whether the balloon 92 has completely inflated by applying the first inflation pressure to the balloon 92 by the first inflation pressure applying means, and second inflation pressure applying means (step S208, the isolator 40, the first auxiliary switching valve 114) for decreasing the pressure Pb in the balloon 92 by applying the second inflation pressure to the balloon 92 when the completely inflation estimating means estimates that the balloon 92 has completely inflated. In this case, the second inflation pressure should be substantially equal to and higher the minimum pressure and is lower than the first inflation pressure applied by the first inflation pressure applying means. Therefore, the quick inflation response can be assured upon the balloon inflation, while the quick deflation response can be assured for the next deflation, thereby enabling to improve the balloon pressure response.

The balloon pump driving apparatus 10 according to the second embodiment of the present invention includes the deflation judging means (step S214) for judging whether it is necessary to deflate the balloon 92 based upon the inputted bio signal, the first deflation pressure applying means (step S215, the isolator 40, the pressure control valve 52) for applying the first deflation pressure to the balloon 92, which is lower than the maximum pressure at which the balloon 92 can be maintained at the deflated condition, when the deflation judging means judges that it is necessary to deflate the balloon 92, the complete deflation estimating means (step S216) for estimating whether the balloon 92 has completely deflated by applying the pressure to the balloon 92 by the first deflation pressure applying means, and the second deflation pressure applying means (stop S217, the isolator 40, the first auxiliary switching valve 114) for increasing the pressure Pb in the balloon 92 by applying the second deflation pressure to the balloon 92 when the completely deflation estimating means estimates that the balloon 92 has completely deflated. In this case, the second deflation pressure should be substantially equal to and lower than the maximum pressure and is higher than the first deflation pressure applied by the first deflation pressure applying means. Therefore, the quick deflation response can be assured upon the balloon inflation, while the quick inflation response can be assured for the next inflation, thereby enabling to improve the balloon pressure response.

According to the second embodiment of the present inventions in response to the opening operation of the pressure control valve 52 after accumulating the first inflation pressure P1 in the isolator 40, the first inflation pressure P1 is applied to the balloon 92 such that the balloon 92 is inflated. In the elapsed time T1 set after the opening operation of the pressure control valve 52, the pressure control valve 52 is closed. The controller 70 then judges whether the balloon 92 has completely inflated. When the controller 70 judges that the balloon 92 has completely inflated, the communication between the auxiliary reservoir tank 111 and the balloon 92 is established by opening the first auxiliary switching valve 114. Although the communication between the auxiliary reservoir tank 111 and the balloon 92 is established, the pressure Pr in the auxiliary reservoir tank 111 has been set at the predetermined second inflation pressure P5. Therefore, the pressure Pb in the balloon 92 is decreased by applying the second inflation pressure P5 to the balloon 92. The pressure control valve 52 is then closed in the elapsed time T2. As described above, according to the second embodiment of the present invention, the balloon 92 can be applied with a pressure higher than the minimum pressure required for inflating the balloon 92 even when the balloon 92 has been completely inflated. Therefore, the balloon 92 can be inflated at a further faster inflating speed.

When the controller 70 estimates that the balloon 92 has completely inflated, the pressure in the balloon 92 is decreased by applying the second inflation pressure to the balloon 92. Therefore, the pressure differential upon the following deflation can be decreased, thereby not hindering the following quick deflation. As described above, according to the second embodiment of the present invention, the quick inflation response upon the balloon inflation can be ensured, while the quick balloon deflation response upon the following balloon deflation can be ensured. Overall, the balloon inflating/deflating response can be effectively improved. Further, the pressure Pr in the auxiliary reservoir tank 111 is set or adjusted at a predetermined pressure level by the auxiliary reservoir pressure setting control. Therefore, the auxiliary reservoir tank 111 can be employed as a pressure supplying source for supplying a predetermined pressure level to the balloon 92.

During the balloon inflation step, the second auxiliary switching valve 115 is opened after closing the first auxiliary switching valve 114 (step S210), wherein the communication between the auxiliary reservoir tank 111 and the isolator 40 is established. Therefore, the pressure Pr in the auxiliary reservoir tank 111 is set at the predetermined pressure P6 for the balloon deflation step (steps S211, S212, S213). Further, during the balloon deflation step, the second auxiliary switching valve 115 is opened (step S222) after closing the first auxiliary switching valve 114 (step S220), wherein the communication between the auxiliary reservoir tank 111 and the isolator 44 is established. Therefore, the pressure Pr in the auxiliary reservoir tank 111 can be set at the predetermined pressure P5 for the balloon inflation step (steps S222, S223, S224). That is, while the inflation step has been performed, the pressure Pr in the auxiliary reservoir tank 111 is set at the pressure P6 for the balloon deflation. While the deflation step has been performed, the pressure Pr in the auxiliary reservoir lank 111 is set at the pressure P5 for the balloon inflation. As described above, according to the second embodiment of the present invention, the pressure in the auxiliary reservoir tank 111 can be adjusted through the balloon pumping system 200. Therefore, there is no need to additionally provide an apparatus for adjusting the pressure Pr in the auxiliary reservoir tank 111, thereby enabling to downsize the system.

Further, according to the second embodiment of the present invention, the pressure supply can be performed through a system having the isolator 40 and the other system having the auxiliary reservoir tank 111. Therefore, the balloon pumping system 200 can effectively function even when extra systole or premature beat is caused due to abnormal cardiac rhythms. For example, if a signal for the extra systole interrupts when the balloon 92 has inflated with the pressure control valve 52 opened at step S203 illustrated in FIG. 6A, the pressure control valve 52 is closed, and the second auxiliary switching valve 114 is opened, wherein the communication between the balloon 92 and the auxiliary reservoir tank 111 is established. Therefore, the balloon inflation can be restrained, or the operation by the system 200 can be shifted from the inflation operation to the deflation operation. Then balloon 92 can be then deflated at much faster deflating speed than the normal deflating speed.

According to the second embodiment of the present invention, in response to the opening operation of the pressure control valve 52 after accumulating the first deflation pressure P3 in the isolator 40, the first deflation pressure P3 is applied to the balloon 92, wherein the balloon 92 is deflated. The controller 70 then estimates whether the balloon 92 has completely deflated. When the controller 70 estimates that the balloon 92 has completely deflated, the communication between the auxiliary reservoir tank 111 and the balloon 92 is established by opening the first auxiliary switching valve 114. In this case, although the communication between the auxiliary reservoir lank 111 and the balloon 92 is established, the pressure Pr in the auxiliary reservoir tank 111 has been set at the predetermined second deflation pressure P6. The balloon 92 is applied with the second deflation pressure P6 so that the pressure in the balloon 92 is increased. The pressure control valve 52 is then closed in a predetermined elapsed time. As described above, according to the second embodiment of the present invention, the balloon 92 is applied with a pressure lower than the maximum pressure required for deflating the balloon 92 even when the balloon 92 has been completely deflated. Therefore, the balloon 92 can be deflated at a further faster deflating speed.

Further, when the controller 70 judges that the balloon 92 has completely inflated, the pressure differential upon the next inflation can be reduced by decreasing the pressure Pb in the balloon 92 by applying the second deflation pressure to the balloon 92, thereby not hindering the quick inflation upon the next inflation timing. Therefore, the much faster deflation can be assured, and the quick inflation response is not hindered, thereby enabling to improve the balloon pressure response.

Next, following explanation will be given for explaining the balloon pump driving apparatus according to a third embodiment of the present invention. The structure of the balloon pump driving system according to the third embodiment is substantially identical to the structure illustrated in FIG. 4, so that the explanation of the structure will be omitted herein.

Figure 7:
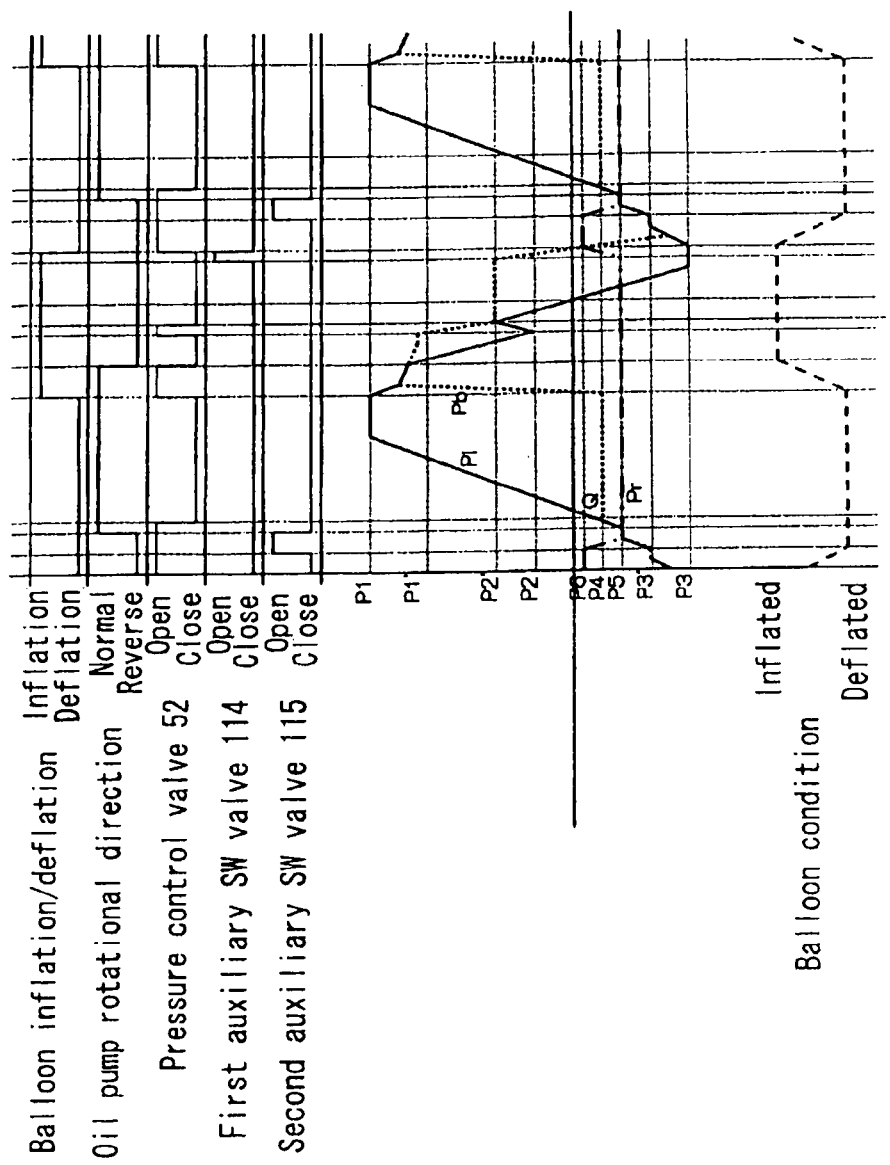
FIG. 7 is a timing chart for explaining transitions of the timing for inflating and deflating the balloon, the inflated and deflated condition of the balloon, the rotational direction of the oil pump, the timing for switching the pressure control valve, the timings for switching first and second switching valves, the pressure in the output chamber, the pressure applied to the balloon, and a pressure in an auxiliary reservoir tank according to the third embodiment of the present invention.
Figure 8A:
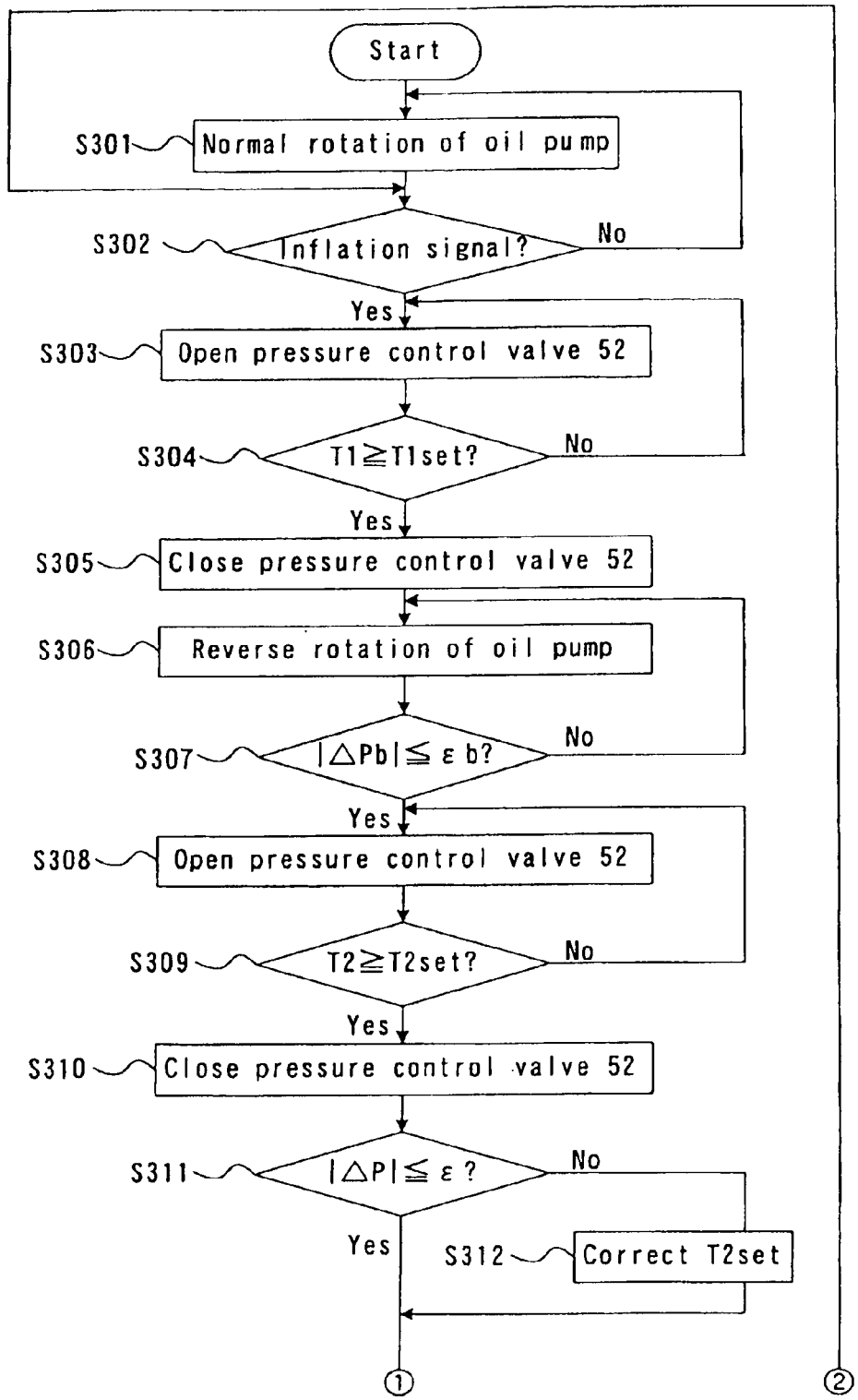
FIGS. 8A and 8B are a main flowchart of the controller for inflating and deflating the balloon by the balloon pumping system according to the third embodiment of the present invention.
Figure 8B:
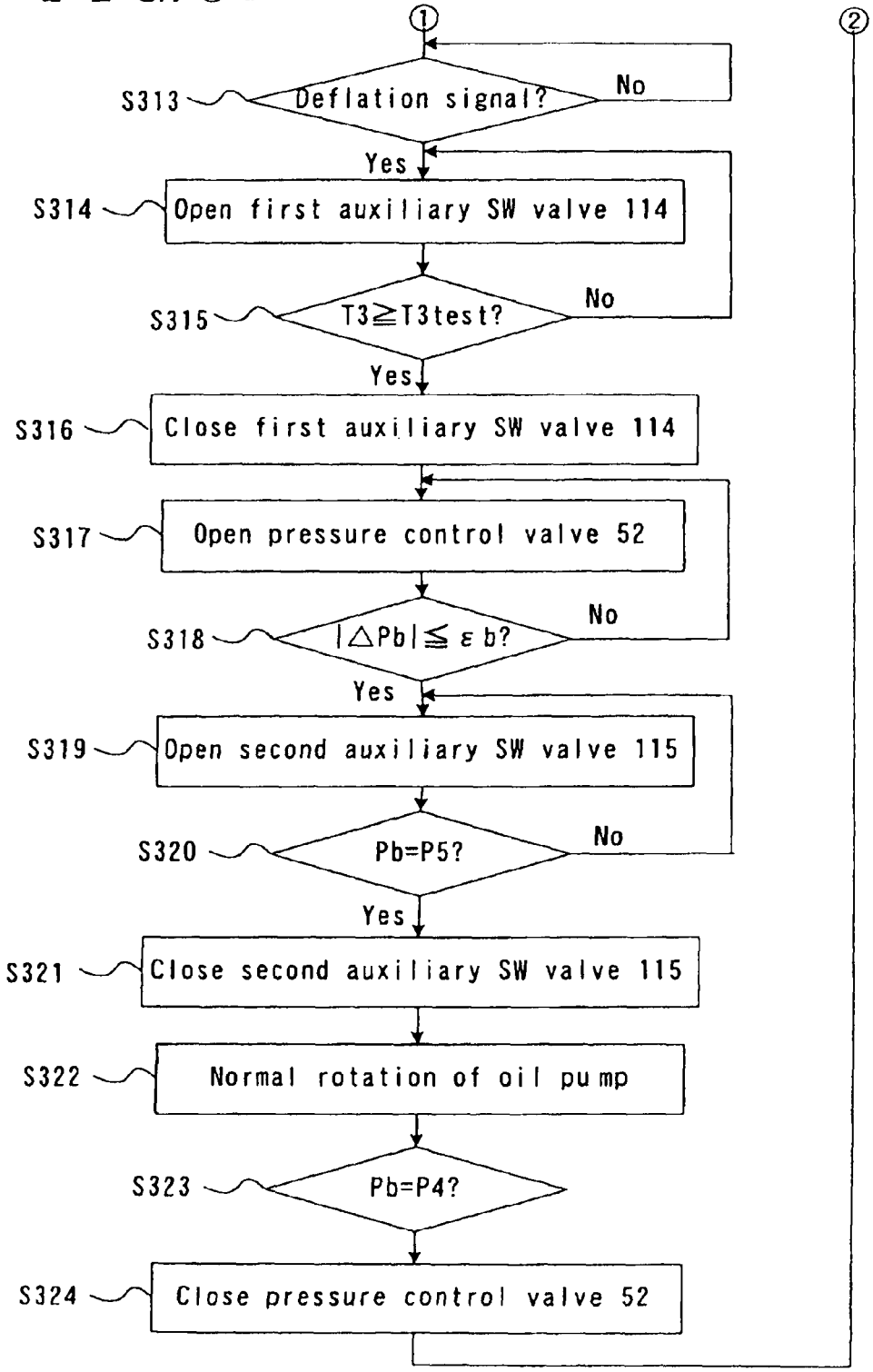

The method of pumping the balloon is briefly described hereinbelow. In order to inflate the balloon 92, the pressure in the isolator 40 and the switching operation of the pressure control valve 52 are controlled. In order to deflate the balloon 92, the pressure in the isolator 40 and the auxiliary reservoir tank 111, and the switching operations of the pressure control valve 52 and the first auxiliary switching vale 114 are controlled. At the point Q in FIG. 7, the oil pump 30 is driven for rotation in the normal rotational direction with the closed pressure control valve 52 (step S301). Therefore, the pressure Pi in the output chamber 44 is increased, so that the pressure Pi is increased up to the first inflation pressure P1. The controller 70 judges the presence or absence of the inflation signal for the balloon 92 (step S302). When the inflation signal is detected, the pressure control valve 52 is opened (step S303). The communication between the output chamber 44 and the balloon 92 is established in response to the opening operation of the pressure control valve 52, wherein the balloon 92 is applied with the first inflation pressure P1 so that the balloon 92 is inflated.

The controller 70 then judges whether the opening period T1 of the pressure control valve 52 reached the set period T1set (step S304). The controller 70 closes the pressure control valve 52 (step S305). The oil pump 30 is driven for rotation in the reverse direction (step S306), wherein the pressure in the output chamber 44 is decreased. Although the balloon 92 has not completely inflated yet when the pressure control valve 52 is closed, the balloon 92 is inflated as time goes and is completely inflated eventually. When the balloon 92 approaches the completely inflated condition, the amount of helium gas to flow to the balloon 92 is gradually decreased, and the pressure Pb in the balloon 92 becomes a constant pressure value. The controller 70 judges whether the balloon 92 has completely inflated based upon the pressure change rate ÄPb with time (step S307). As explained in FIG. 7, the pressure Pb becomes approximately constant at the pressure P1'. The pressure P1' is higher than the pressure value at which the balloon 92 is generally inflated. According to the third embodiment of the present invention, the balloon 92 is inflated at the pressure P2'. As described above, the balloon 92 has been applied with the pressure higher than the conventional pressure level even when the balloon 92 is completely inflated. Therefore, the balloon 92 can be quickly inflated. The pressure control valve 52 is opened again when the balloon 92 is estimated to have completely inflated (step S308).

When the pressure control valve 52 is opened again, the pressure Pi in the output chamber 44 is decreased and becomes lower than the pressure P2. In response to the opening operation of the pressure control valve 52, the helium gas is introduced from the balloon 92 to the output chamber 44, wherein the applied pressure Pb to the balloon 92 is decreased. The controller 70 then judges that the opening period T2 has reached the set period T1set (step S309). The pressure control valve 52 is then closed in the set period T2set (step S310). Therefore, the pressure Pb in the balloon 92 can be maintained at the pressure P2', wherein the balloon 92 can be inflated at this pressure level.

Upon the inflation of the balloon 92, the balloon 92 has been initially applied with the pressure P1 that is relatively high. Therefore, the balloon, 92 can be inflated at a high inflating speed. When the balloon 92 is shifted to the completely inflated condition, the pressure Pb of the balloon 92 is decreased down to the pressure P2'. Therefore, the time for applying the high pressure to the balloon 92 is decreased, wherein the durability of the balloon 92 can be improved. Further, the pressure differential of the balloon internal pressure can be decreased when the balloon 92 is next deflated, thereby enabling to improve the balloon deflation response for the next deflation.

The controller 70 judges at step S311 whether the absolute pressure value ÄP is within the predetermined range å. The set period T2set is corrected based upon the judgment result at step S311 (step S312). The controller then judges the presence or absence of the deflation signal (step S313). When the deflation signal is detected at step S313, the first auxiliary switching valve 114 is opened (step S314). In response to the opening operation of the first auxiliary switching valve 114, the communication between the auxiliary reservoir tank 111 and the balloon 92 is established. The auxiliary reservoir tank 111 has been set at the pressure P5. The pressure P5 is lower than the pressure P2' applied to the balloon 92 immediately before opening the first auxiliary switching valve 114 at step S314. Therefore, the helium gas is introduced from the balloon 92 to the auxiliary reservoir tank 111, wherein the pressure Pb applied to the balloon 92 is decreased.

The controller 70 judges whether an opening period T3 has reached a set period T3set after opening the first auxiliary switching valve 114 (step S315). When the opening period T3 has reached the set period T3set, the first auxiliary switching valve 114 is closed (step S316). Through steps S315 and S316, the pressure Pr in the auxiliary reservoir tank 111 is set at a predetermined pressure P6. The pressure control valve 52 is then opened (step S317). In this case, the communication between the output chamber 44 and the balloon 92 is established. The pressure Pi in the output chamber 44 is decreased in response to the reserve rotation of the oil pump 30 immediately before opening the pressure control valve 52 at step S317. The pressure Pi in the output chamber 44 is hence maintained at the first deflation pressure P3 that is lower than the normal deflation pressure. Therefore, in response to the opening operation of the pressure control valve 52 at step S317, the helium gas in the balloon 92 is introduced to the output chamber 44, wherein the pressure Pb applied to the balloon 92 is rapidly decreased. The balloon 92 has not completely deflated yet immediately after opening the pressure control valve 52. As time goes, the balloon 92 is deflated and is completely deflated eventually. When the balloon 92 approaches the completely deflated condition, the amount of helium gas flowing from the balloon 92 is reduced. Therefore, the pressure Pb is maintained at a constant pressure level. The controller 70 then judges the balloon 92 has completely deflated based upon the pressure change rate APb with time (step S318). As explained in FIG. 7, the pressure Pb becomes approximately constant at the pressure P3'. The pressure P3' is greater than the pressure at which the balloon 92 is generally deflated. According to the third embodiment of the present invention, the pressure, at which the balloon 92 is generally deflated, is the pressure P4. As described above, the balloon 92 has been applied with the pressure lower than the conventional applied pressure even when the balloon 92 has completely deflated. Therefore, the balloon 92 can be quickly deflated. The second auxiliary switching valve 115 is opened when the balloon 92 is estimated to have completely deflated (step S319). Therefore, the communication between the auxiliary reservoir tank 111 and the output chamber 44 is established.

The controller 70 judges whether the pressure Pb has reached the predetermined pressure P5 (step S320). When the pressure Pb is judged to have reached the predetermined pressure P5, the second auxiliary switching valve 115 is closed (step S321). Therefore, the communication between the auxiliary reservoir tank 111 and the output chamber 44 is interrupted, wherein the pressure Pr in the auxiliary reservoir tank 111 is set at the predetermined pressure P5.

The oil pump 30 is driven for rotation in the normal direction after closing the second auxiliary switching valve 115 (step S322). The diaphragm spring in the isolator 40 is moved so that the pressure in the output chamber 44 can be increased. In this case, the pressure control valve 52 has been opened. Therefore, the pressure Pb applied to the balloon 92 is increased in response to the pressure increase in the output chamber 44. The controller 70 then judges whether the pressure Pb has reached the second inflation pressure P4 (step S323). When the pressure Pb is judged to have reached the second inflation pressure P4, the pressure control valve 52 is dosed (step S324). The program then returns to step S302.

As described above, upon deflation of the balloon 92, the communication between the auxiliary reservoir tank 111 and the balloon 92 is established, wherein the pressure Pb in the balloon 92 is first decreased. Next, the balloon 92 is applied with the pressure P3 which is much lower, wherein the pressure Pb in the balloon 92 is decreased. Therefore, the balloon 92 can be quickly deflated. Further, in response to the communication between the auxiliary reservoir tank 111 and the output chamber 44, the helium gas in the auxiliary reservoir tank 111 is drawn back to the output chamber 44, wherein the pressure Pr in the auxiliary reservoir tank 111 can be brought back to the pressure required for the next deflation. Further, the pressure Pb in the balloon 92 can be maintained al the pressure P4 that is the second deflation pressure, wherein the balloon 92 can be prepared for the next inflation.

Further, the second auxiliary switching valve 115 communicates between the auxiliary reservoir tank 111 and the isolator 40. Therefore, the pressure Pr in the auxiliary reservoir tank 111 is set or adjusted at the predetermined pressure by opening/closing the second auxiliary switching valve 115 at a predetermined timing, or the pressure Pr the auxiliary reservoir tank 111 can be adjusted.

Figure 9:
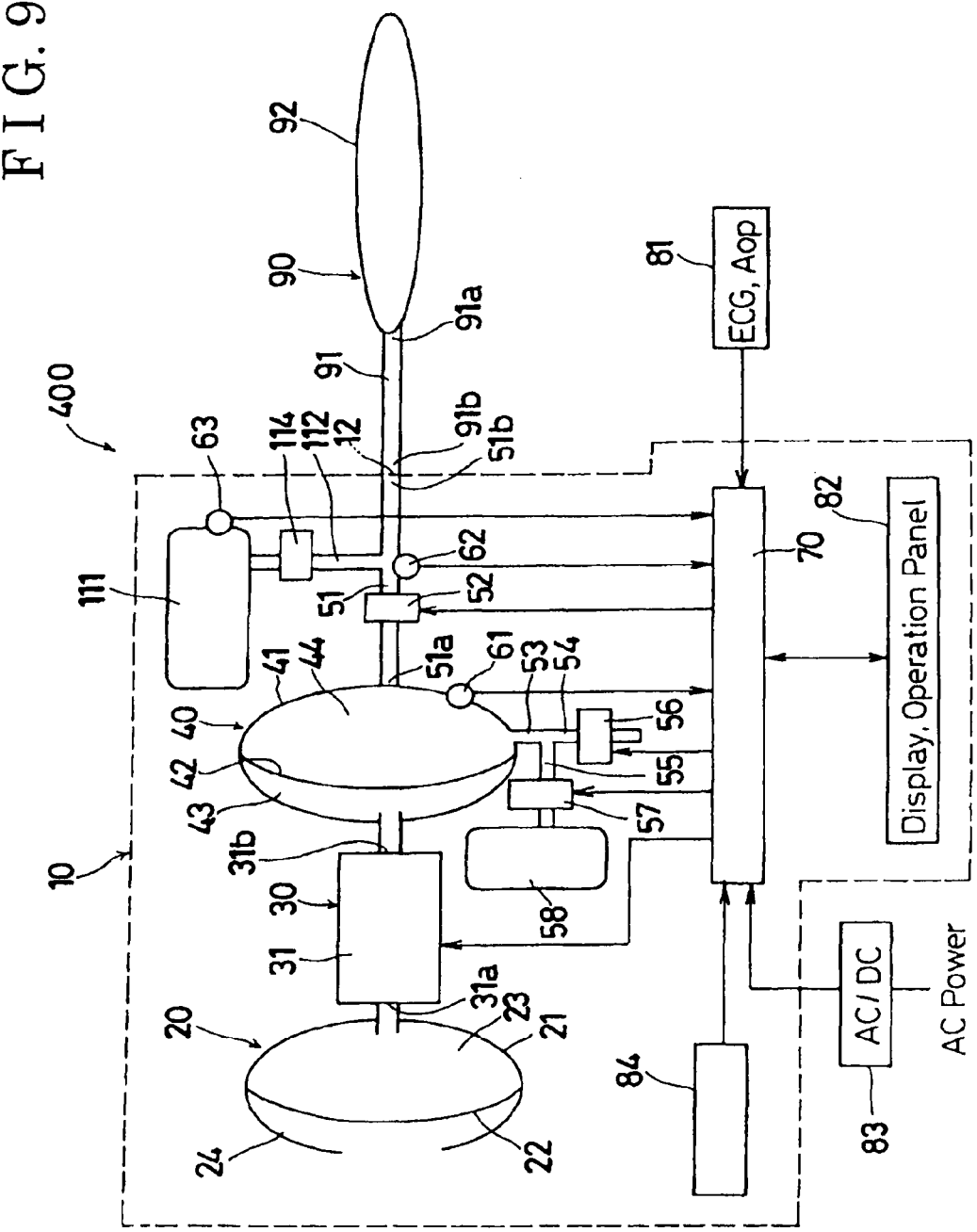
FIG. 9 is a schematic view illustrating a balloon pumping system according to a fourth embodiment of the present invention.

Next, following explanation will be given for explaining the balloon pump driving apparatus according to a fourth embodiment of the present invention. The structure of the balloon pump driving apparatus is illustrated in FIG. 9. The structure thereof is similar to the system illustrated in FIG. 4. However, according to the fourth embodiment, there is not the conduit connecting the auxiliary reservoir tank 111 and the output chamber provided. Further, there is not the second auxiliary switching valve 115. The other structure of the balloon pump driving apparatus according to the fourth embodiment is substantially identical to the one according to the third embodiment, so that the detailed explanation will be omitted herein.

In the same manner as the second embodiment of the present invention, when the balloon 92 is inflated, the relatively high pressure is initially applied to the balloon 92 and is decreased by use of the auxiliary reservoir tank 111. When the balloon 92 is deflated, the relatively low pressure is initially applied to the balloon 92 and is increased by use of the auxiliary reservoir tank 111. However, according to the fourth embodiment of the present invention, the pressure in the auxiliary reservoir tank 111 to be applied to the inflating balloon 92 is set to be substantially equal to the deflation pressure of the balloon 92. Further, the pressure in the auxiliary reservoir tank 111 to be applied to the deflating balloon 92 is set to be substantially equal to the inflation pressure of the balloon 92. Therefore, the step for adjusting the pressure Pr in the auxiliary reservoir tank 111 can be omitted.

Figure 10:
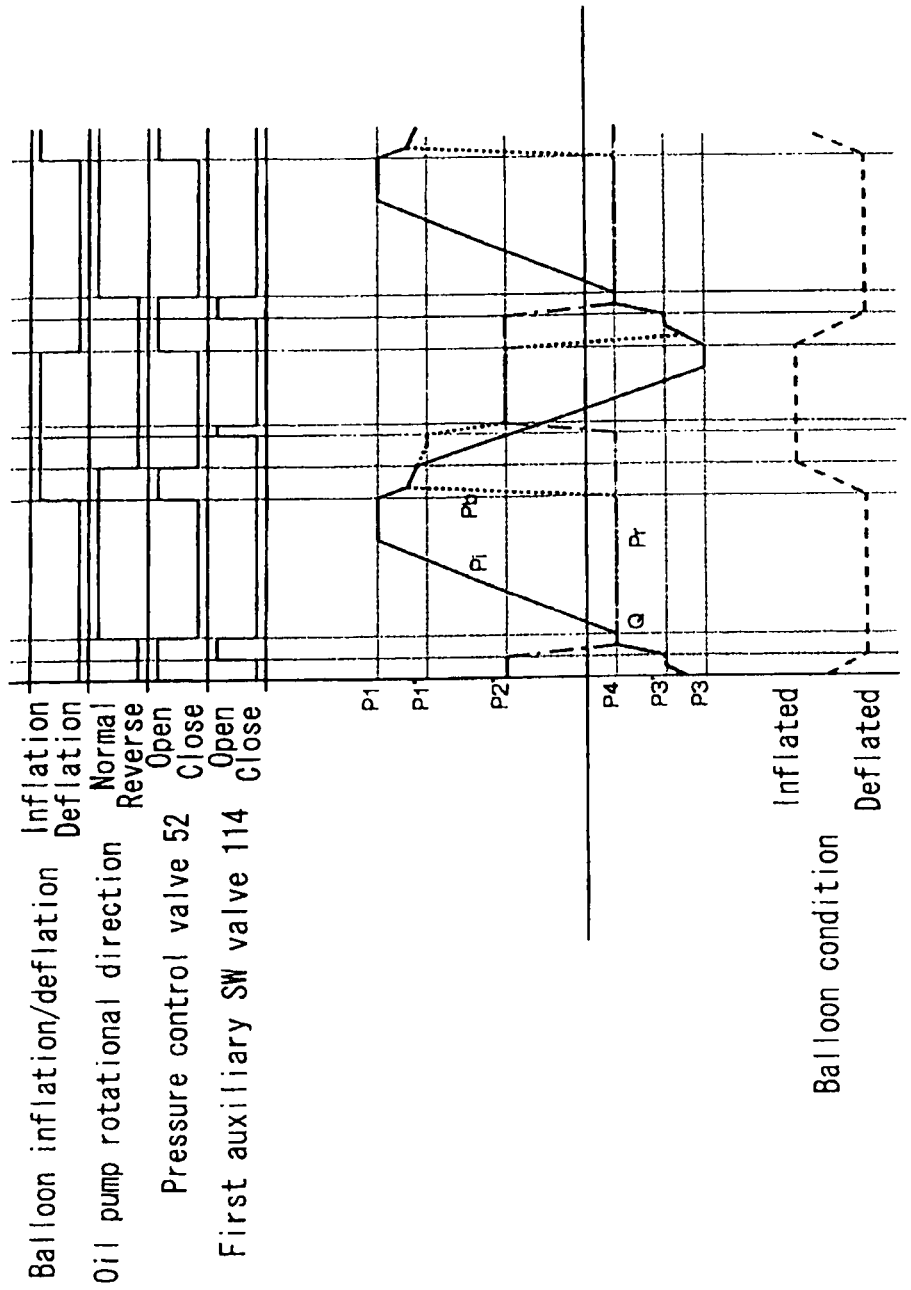
FIG. 10 is a timing chart for explaining transitions of the timing for inflating and deflating the balloon, the deflated and deflated condition of the balloon, the rotational direction of the oil pump, the timing for switching the pressure control valve, the timing for switching the first switching valve, the pressure in the output chamber, the pressure applied to the balloon, and a pressure in an auxiliary reservoir tank according to the fourth embodiment of the present invention.
Figure 11A:
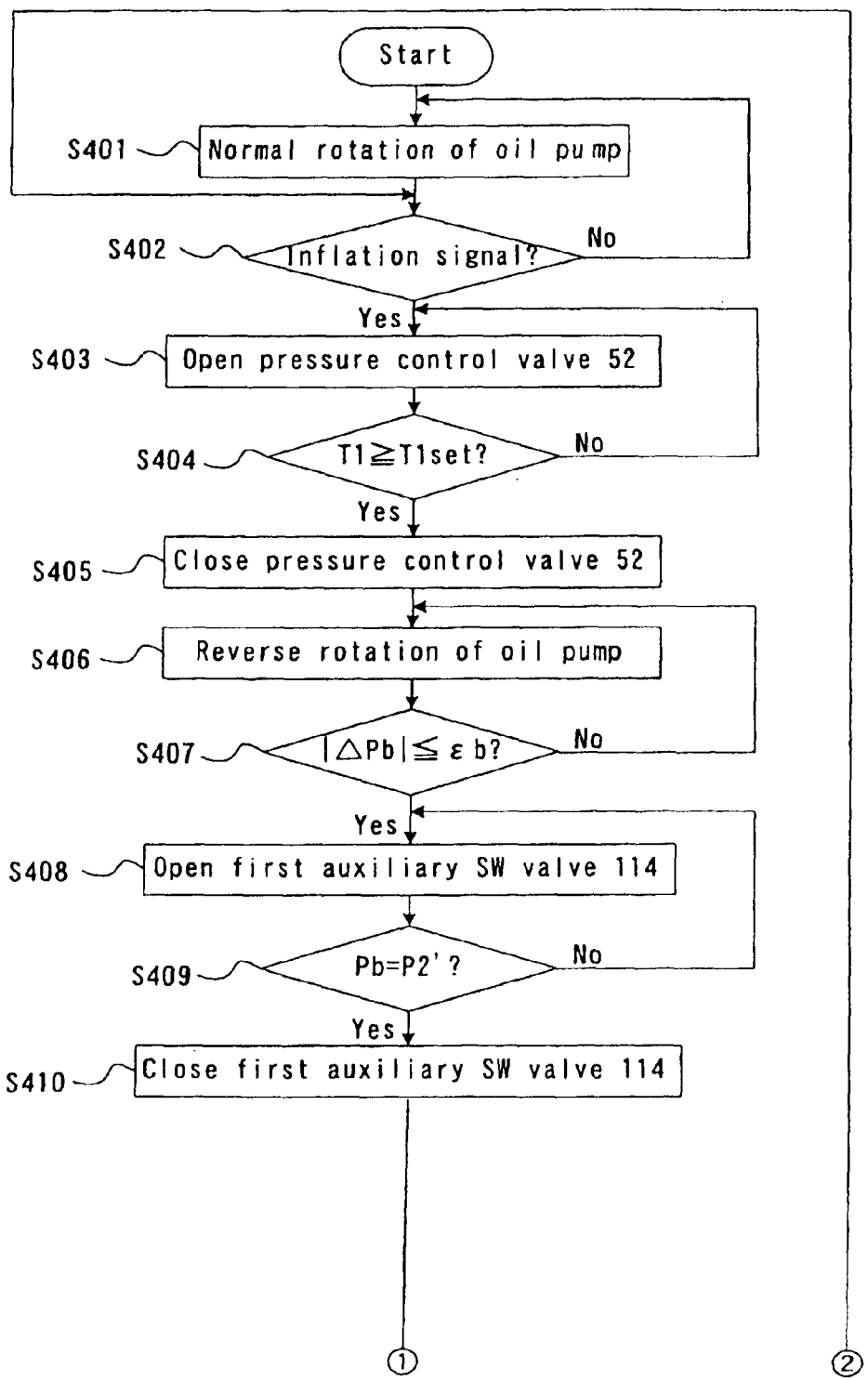
FIGS. 11A and 11B are a main flowchart of the controller for inflating and deflating the balloon by the balloon pumping system illustrated in FIG. 9.
Figure 11B:
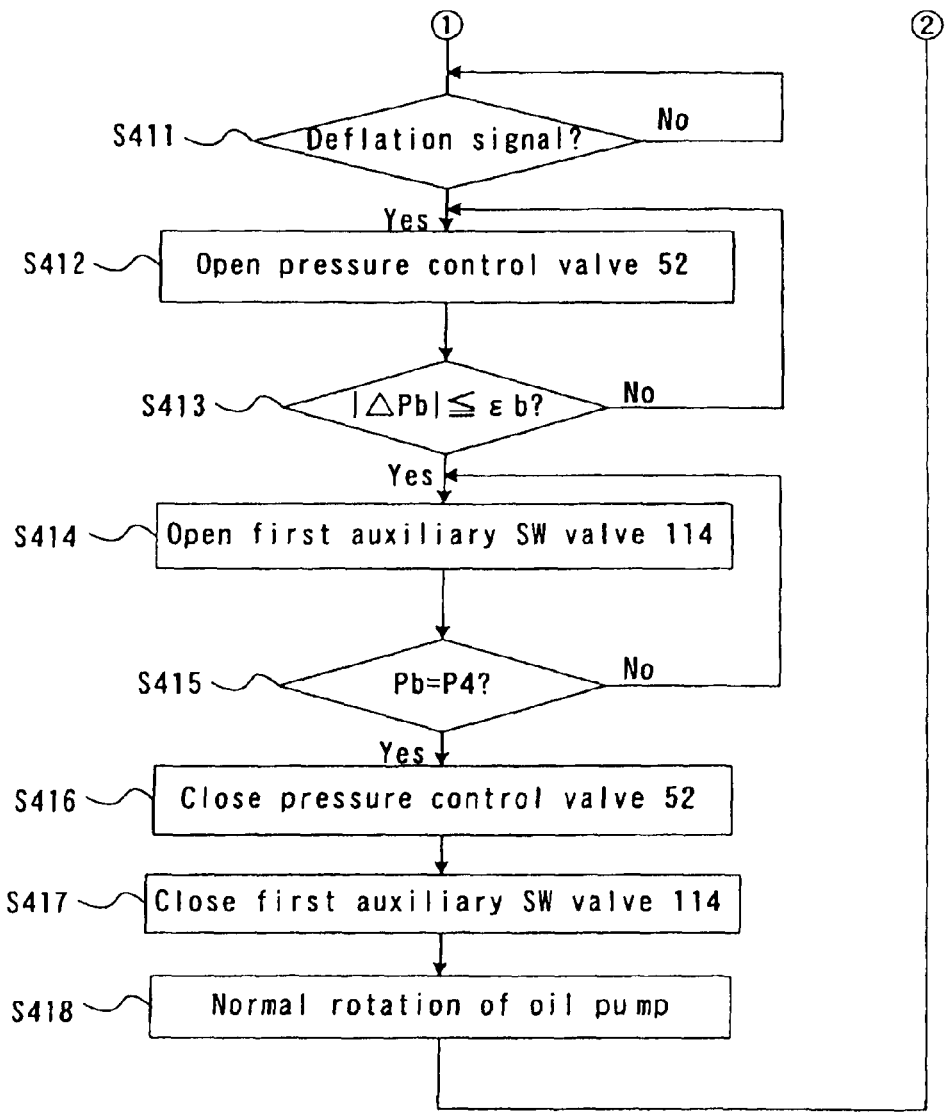

At the point Q in FIG. 10, the oil pump 30 is driven for rotation in the normal rotational direction with the closed pressure control valve 52 (step S401). Therefore, the pressure Pi in the output chamber 44 is increased, so that the pressure Pi is increased up to the first inflation pressure P1. The controller 70 judges the presence or absence of the inflation signal for the balloon 92 (step S402). When the inflation signal is detected, the pressure control valve 52 is opened (step S403). The communication between the output chamber 44 and the balloon 92 is established in response to the opening operation of the pressure control valve 52, wherein the balloon 92 is applied with the first inflation pressure P1 so that the balloon 92 is inflated.

The controller 70 then judges whether the opening period T1 of the pressure control valve 52 reached the set period T1set (step S404). The controller 70 closes the pressure control valve 52 in the period T1set (stop S405). The oil pump 30 is driven for rotation in the reverse direction (step S406), wherein the pressure in the output chamber 44 is decreased. Although the balloon 92 has not completely inflated yet when the pressure control valve 52 is closed, the balloon 92 is inflated as time goes and is completely inflated eventually. When the balloon 92 approaches the completely inflated condition, the amount of helium gas to flow to the balloon 92 is gradually decreased, and the pressure Pb in the balloon 92 becomes a constant pressure value. The controller 70 judges whether the balloon 92 has completely inflated based upon the pressure change rate $\overline{\Delta Pb}$ with time (step S407). As explained in FIG. 10, the pressure Pb becomes approximately constant at the pressure P1'. The pressure P1' is generally higher than the pressure value at which the balloon 92 is generally inflated. According to the fourth embodiment of the present invention, the balloon 92 is inflated at the pressure P2'. As described above, the balloon 92 has been applied with the pressure higher than the conventional pressure level even when the balloon 92 has completely inflated. Therefore, the balloon 92 can be quickly inflated. The first auxiliary switching valve 114 is opened when the balloon 92 is estimated to have completely inflated (step S408).

When the first auxiliary switching valve 114 is opened (step S408), the communication between the auxiliary reservoir tank 111 and the balloon 92 is established. The pressure in the auxiliary reservoir tank 111 has been set at the pressure P4 until a timing immediately before the opening operation of the first auxiliary switching valve 114 at step S408. The pressure P4 is substantially equal to the second deflation pressure P4 that is described later. The pressure P4 is lower than the current pressure Pb in the balloon 92. Therefore, in response to the opening operation of the first auxiliary switching valve 114, the helium gas is introduced from the balloon 92 to the auxiliary reservoir tank 111. Therefore, the pressure Pb applied to the balloon 92 is rapidly decreased. The controller 70 then judges whether the pressure Pb has reached the second inflation pressure P2' (step S409). When the pressure Pb is judged to have reached the second inflation pressure P2', the first auxiliary switching valve 114 is closed (step S410). Therefore, the pressure Pb in the balloon 92 can be maintained at the pressure P2', and the inflation of the balloon 92 can be continued at the pressure P2'. Further, the pressure Pr in the auxiliary reservoir tank 111 is set at the pressure P2'.

As described above, when the balloon 92 is inflated, the balloon 92 is initially applied with the pressure P1 that is high. Therefore, the balloon 92 can be quickly inflated. Further, the pressure Pb of the balloon 92 is decreased down to the pressure P2' when the balloon 92 is completely inflated. Therefore, the time for applying the high pressure to the balloon 92 can be shortened, wherein the durability of the balloon 92 can be extended. Further, the pressure differential in the balloon 92 can be reduced when the balloon 92 is next deflated, thereby enabling to improve the deflation response for the next balloon deflation.

After closing the first auxiliary switching valve 114 at step S410, the controller 70 judges whether the inflation signal has been detected (step S411). When the inflation signal has been detected, the pressure control valve 52 is opened (step S412), wherein the communication between the balloon 92 and the output chamber 44 is established. The pressure Pi in the output chamber 44 has been sufficiently decreased in response to the reverse rotation of the oil pump 30 until timing before the opening operation of the first auxiliary switching valve 114 at step S411. Further, the pressure Pi in the output chamber 44 is brought down to the first deflation pressure P3 that is sufficiently low. Therefore, in response to the opening operation of the pressure control valve 52, the helium gas is introduced from the balloon 92 to the output chamber 44. Therefore, the pressure Pb of the balloon 92 is decreased.

The controller 70 judges whether the pressure change rate $\overline{\Delta Pb}$ of the pressure Pb for the balloon 92 is within the predetermined range åb (step S413). Therefore, the controller 70 can judge whether the balloon 92 has completely deflated. When the controller 70 judges that the balloon has completely deflated, the first auxiliary switching valve 114 is opened (step S414), wherein the communication between the auxiliary reservoir tank 111 and the balloon 92 is established. The pressure Pr in the auxiliary reservoir tank 111 has been set at the pressure P2' until a timing immediately before the opening operation of the first auxiliary switching valve 114. The pressure P2' is substantially equal to the second inflation pressure P2'. The pressure P2' is higher than the pressure Pb of the balloon 92. Therefore, in response to the opening operation of the first auxiliary switching valve 114, the helium gas flows from the auxiliary reservoir tank 111 to the balloon 92, wherein the pressure Pb to be applied to the balloon 92 is rapidly increased. The controller 70 then judges whether the pressure Pb has reached the second inflation pressure P4 (step S415). When the controller 70 judges that the pressure Pb has reached the second inflation pressure P4, the pressure control valve 52 is closed (step S416). Further, the first auxiliary switching valve 114 is closed (step S417). Therefore, the pressure Pb of the balloon 92 can be maintained at the pressure P4, and the balloon 92 can be continuously inflated at the pressure P4. Further, the pressure Pr of the auxiliary reservoir tank 111 is set at the pressure P4. The oil pump 30 is driven for rotation in the normal direction (step S418). The program then returns to step S402.

As described above, when the balloon 92 is inflated, the balloon 92 is initially applied with the pressure P1 that is high. Therefore, the balloon 92 can be quickly inflated. Further, the pressure Pb of the balloon 92 is reduced down to the pressure P1' when the balloon 92 is shifted to the completely inflated condition. Therefore, the time for applying the balloon 92 with the high pressure can be reduced, thereby enabling to extend the durability of the balloon 92. Further, the pressure differential in the balloon 92 can be decreased for the next deflation, thereby enabling to improve the balloon deflation response for the next balloon deflation. Further, according to the fourth embodiment of the present invention, the second auxiliary switching valve 115 is not provided. Therefore, the pressure Pb and Pr are adjusted only by use of the first auxiliary switching valve 114. Therefore, the size of the balloon pump driving apparatus can be reduced.

The principles, embodiments and modes of operation of the present invention have been described in the foregoing specification and drawings. However, the invention which is intended to be protected is not to be construed as limited to the particular embodiments disclosed. Further, the embodiments described herein are to be regarded as illustrative rather than restrictive. Plural objectives are achieved by the present invention, and yet there is usefulness in the present invention as far as one of the objectives are achieved Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. A balloon pumping method of changing a balloon between a deflated condition and an inflated condition in a blood vessel at a predetermined timing, comprising:
    a first step of applying a pressure into the balloon so as to inflate the balloon from the deflated condition into the inflated condition, and of setting a pressure in the balloon at a first pressure value which is higher than a minimum pressure value capable of preventing the balloon in the inflated condition from being deflated, and which is lower than a maximum pressure value capable of maintaining the inflated condition of the balloon;
    a second step, after the first step, of detecting that the balloon has been changed into the inflated condition; and
    a third step, after the second step, of releasing the pressure in the balloon, and setting the pressure in the balloon at a second pressure value which is substantially equal to or higher than the minimum pressure value, and which is lower than the first pressure value.

2. The balloon pumping method according to claim 1, further comprising:
    a fourth step, after the third step, of decreasing the pressure in the balloon so as to deflate the balloon from the inflated condition into the deflated condition.

3. The balloon pumping method according to claim 1, wherein
    the second step includes detecting that the balloon has been changed into the inflated condition when a pressure change rate of the pressure in the balloon becomes zero or within a predetermined range.

4. The balloon pumping method according to claim 1, further comprising:
    a step, before the first step, of setting a pressure in an output chamber at a third pressure value higher than the first pressure value, the output chamber capable of being communicated with the inside of the balloon,
    wherein, in the first step, the output chamber and the inside of the balloon are communicated with each other for a predetermined period, and the pressure in the output chamber is applied into the balloon, thereby setting the pressure in the balloon at the first pressure value.

5. The balloon pumping method according to claim 4, further comprising:
    a fourth step, after the third step, of decreasing the pressure in the balloon so as to deflate the balloon from the inflated condition into the deflated condition.

6. The balloon pumping method according to claim 4, wherein
    the second step includes detecting that the balloon has been changed into the inflated condition when a pressure change rate of the pressure in the balloon becomes zero or within a predetermined range.

7. The balloon pumping method according to claim 4, further comprising:
    a step, between the first step and the third step, of setting the pressure in the output chamber at a fourth pressure value lower than the second pressure value,
    wherein, in the third step, the output chamber and the inside of the balloon are communicated with each other for a predetermined period, and the pressure in the balloon is released into the output chamber, thereby setting the pressure in the balloon at the second pressure value.

8. The balloon pumping method according to claim 1, further comprising:
    a step, between the first step and the third step, of setting a pressure in a tank at a fourth pressure value lower than the second pressure value, the tank capable of being communicated with the inside of the balloon,
    wherein, in the third step, the tank and the inside of the balloon are communicated with each other for a predetermined period, and the pressure in the balloon is released into the tank, thereby setting the pressure in the balloon at the second pressure value.

9. The balloon pumping method according to claim 1, wherein
    in the first step, the pressure is applied into the balloon by supplying gas into the balloon, and
    in the third step, the pressure in the balloon is released by releasing gas in the balloon.

* * * * *